United States Patent [19]

Konno et al.

[11] Patent Number: 5,608,451
[45] Date of Patent: Mar. 4, 1997

[54] ENDOSCOPE APPARATUS

[75] Inventors: Mitsujiro Konno, Hoya; Akira Hasegawa, Akishima, both of Japan

[73] Assignee: Olympus Optical Co., Ltd., Tokyo, Japan

[21] Appl. No.: 394,820

[22] Filed: Feb. 27, 1995

[30] Foreign Application Priority Data

Mar. 11, 1994 [JP] Japan ................... 6-041395
Nov. 14, 1994 [JP] Japan ................... 6-279249

[51] Int. Cl.⁶ .................. A61B 1/04; A61B 1/06; H04N 7/18
[52] U.S. Cl. .................. 348/69; 348/73; 600/109
[58] Field of Search .................. 348/65, 68, 69, 348/73; 600/109, 110, 111, 112, 160, 180; H04N 7/18

[56] References Cited

U.S. PATENT DOCUMENTS

| | | | |
|---|---|---|---|
| 4,318,132 | 3/1982 | Machida | 348/229 |
| 4,791,480 | 12/1988 | Muranaka | 348/69 |
| 4,967,269 | 10/1990 | Sasagawa et al. | 348/69 |
| 5,159,380 | 10/1992 | Furuya et al. | 354/415 |
| 5,237,403 | 8/1993 | Sugimoto | 348/69 |

*Primary Examiner*—Howard W. Britton
*Attorney, Agent, or Firm*—Cushman, Darby & Cushman IP Group of Pillsbury Madison & Sutroo LLP

[57] ABSTRACT

An endoscope apparatus includes an optical system for forming an image of an object; a solid-state image sensor for receiving the image formed by the optical system; an illuminating device for irradiating the object with illuminating light; a light control device for changing the brightness of the illuminating light; a stop device whose aperture is variable, disposed in the optical system; a detecting device for detecting the brightness of the image of the object; and a control device for controlling the stop device and the light control device so that the intensity of a signal output from the solid-state image sensor is kept nearly constant in accordance with brightness information derived from the detecting device. In this way, the endoscope apparatus always maintains the optimum brightness of the image and ensures a practical pan-focus state in which a user's operation load is reduced.

29 Claims, 16 Drawing Sheets

ENDOSCOPE APPARATUS

BACKGROUND OF THE INVENTION

1. Field of the Invention

This invention relates to an endoscope apparatus equipped with an auto-iris device which is capable of changing the aperture size of stop means in response to information on the brightness of an object derived from the intensity of a signal output from a charge coupled device image sensor.

2. Description of Related Art

Some of endoscope apparatus in recent years have been designed so that a TV camera housing a charge coupled device image sensor (which is hereinafter referred simply to as a CCD or a solid-state image sensor) is attached to the connection of a non-flexible endoscope and an image inside a human body is displayed on a monitor for diagnosis and therapy. FIG. 1 shows the entire construction of the imaging system of such an endoscope apparatus. Reference numeral 1 denotes an endoscope (non-flexible endoscope); 2 a TV camera head; 3 a TV camera control unit (CCU); 4 a monitor; and 5 a light source device.

The endoscope 1 includes an objective lens 7 provided with a fixed stop 6, an image transmitting optical system composed of a plurality of relay lenses (three in this figure) 8, 9, and 10, and an observing optical system composed of an eyepiece 11. It further includes a light guide 12 composed of a fiber bundle juxtaposed with the objective lens 7 and the image transmitting optical system. The TV camera head 2 is equipped with an adapter lens 13, a CCD 14, and a signal cable 15 for transmitting an output signal from the CCD 14. The light source device 5 includes a source lamp 16, a source stop (light control means) 17, and a collector lens 18. The endoscope 1 is connected with the light source device 5 by a light guide cable 19.

The light guide cable 19 is such that its one end is connected to the light source device 5 and the other end is connected to the light guide 12 of the endoscope 1 through a connector 21 incorporating coupling lenses 20. Light emitted from the source lamp 16 travels through the source stop 17 and is collected by the collector lens 18 at the entrance end of a fiber bundle 22 encased in the light guide cable 19. The light emerges from the exit end of the fiber bundle 22 and is collected at the entrance end of the light guide 12 by the coupling lenses 20. Subsequently, the light is radiated from the exit end of the light guide 12 toward an object M.

Reflected light from the object M is incident on the objective lens 7 to form the image of the object behind the objective lens 7. The image is transmitted to the front of the eyepiece 11 by the image transmitting optical system while being formed in succession by the respective relay lenses. Light from the image emerges as nearly parallel beams from the eyepiece 11 toward the adapter lens 13 situated inside the TV camera head 2.

When the TV camera head 2, although it can be removed from the eyepiece section of the endoscope 1, is mounted thereto, the adapter lens 13 receives the light from the eyepiece 11 so that the image of the object M is formed on the CCD 14. The output signal from the CCD 14 is supplied through the signal cable 15 to the CCU 3. The CCU 3 has the functions of converting this signal into a particular signal (such as a television signal following the NTSC standard) which can be displayed on the monitor 4, and also of processing various signals when necessary. Furthermore, the CCU 3 is provided with the function of generating various control signals for controlling the entire system. A TV signal output from the CCU 3 is fed to the monitor 4, on which the image of the object M is displayed.

The CCU 3 is adapted to detect the brightness of the reflected light from the object M by making use of the output signal derived from the CCD 14 and to supply an automatic light control driving signal to the light source device 5 so that the reflected light has optimum brightness. With this signal, the source stop 17 is controlled and the amount of light irradiated on the object M is properly adjusted.

Such endoscope apparatus, chiefly used for surgical operation, are attended with intricate work in order that a doctor performs focusing and secures the range of observation during the operation. One of means for solving this problem is to mount an autofocus mechanism on the endoscope apparatus. However, in endoscopes, unlike the case of ordinary photographic cameras, the position of a part observed by a doctor is not necessarily limited to the center of the visual field, and thus it is difficult to bring the doctor's desired part for observation into an accurate autofocus state. In addition, it is also technically difficult to incorporate a focus detecting element in the endoscope with a very small diameter. Hence, in order to ensure the observation range of the endoscope, it is desirable to increase the depth of field and bring about a pan-focus state. Endoscopes are constructed so that the light guide composed of an optical fiber for light transmission is disposed therein and illuminating light is radiated from the distal end portion thereof. When a luminance Bk of the light source is constant, an illuminance E of an object surface is proportional to the square of a distance x between the distal end portion of the endoscope and the object M. Brightness thus changes with the distance x. In order to properly hold the illuminance E, irrespective of the distance x, it is desired that the luminance Bk can always be set to the optimum value (for example, the output which finally becomes 80IRE as a TV signal).

Thus, in the conventional endoscope apparatus, as shown in FIG. 1, the aperture of the stop 6 is fixed in a state where it is stopped down to some extent, and the illuminance E of the object surface varying with the distance x from the distal end portion of the endoscope 1 to the object M has been corrected in such a way that a filter, such as a neutral density (ND) filter, is disposed inside the light source device 5 to change the amount of light of the light source device 5, and thereby an illuminance E' of the image surface of the CCD 14 is made constant.

The relationship between the illuminance E' of the CCD 14 and the distance x in this case is shown in FIG. 2. In this diagram, the axis of ordinates is the illuminance E' of the CCD 14 and the axis of abscissas is the distance x. Curves A to C drawn by broken lines represent how the illuminance E' of the CCD 14 varies with the distance x in the case where the luminance Bk of the light source device 5 and the aperture of the stop 6 are constant.

Calling r the reflectance of the object and NA' the numerical aperture governed by the optical system, the image illuminance E' is given by $$E' \propto r\, Bk\, NA'^2 / x^2 \qquad (1)$$

Thus, in FIG. 2, the improvement of the luminance of the light source brings about a change in the luminance Bk and consequently, the illuminance E' changes as in the curves A to C. This graph shows that the source stop 17 shown in FIG. 1 is controlled so that the amount of illuminating light supplied by the source lamp 16 changes (namely, the luminance of the light source changes) and the illuminance E' varies between the curve A (small in the amount of light) and the curve C (larger in the amount of light) accordingly. In the range of object distances x2 to x3, the control of the amount of light by the source stop 17 is possible, and thus the image illuminance E' can be kept constant. A point a indicates the position where the amount of transmitted light of the source stop 17 is minimized, and when the object is closer (x<x2), the image illuminance E' ceases to be controllable and increases. In contrast to this, a point c is the position of the maximum amount of transmitted light of the source stop 17 and when the object lies farther away, the image illuminance E' decreases. Although the curves of this graph may fluctuate because of the variation of reflectance of the object and the unevenness of light of the source lamp, it is here assumed, for simplicity, that such fluctuation is caused only by a change in luminance of the light source.

Here, it is assumed that the luminance Bk of the light source is constant on a curve B and the aperture of the stop 6 is set to φ1 so that the image illuminance E' of the object at a distance x1 comes to an appropriate image illuminance E'1. Then, the luminance Bk of the light source is controlled so that the illuminance E' becomes the constant value E'1 to shift along the solid line of the graph. In this case, within the region of the points a to c in which the illuminance E' is constant, observations will be made with exactly the same F-number (the aperture φ1 of the stop 6).

In the above-mentioned conventional endoscope apparatus, if the objective optical system is intended to be in a pan-focus state, the aperture of the stop 6 must be diminished and thus brightness becomes insufficient. Consequently, since the aperture φ1 of the stop 6 is determined in view of both the brightness and the depth of field, this system is not said to be advantageous to both. In recent years, however, an auto-iris device (hereinafter referred to as an AI device) in which the aperture of the stop can be changed by an electric signal has become compact in design and low in cost. Thus, the application of the AI device to the attachment TV camera for endoscopes shown in FIG. 1 is being discussed. If the AI device is mounted to the attachment TV camera for endoscopes, the endoscope system mentioned above will have two kinds of means for light control, including light control means with the light source device which is already provided. The AI device, which has a considerable effect on the depth of field as well as on brightness, involves the difficulty, depending on light control techniques, that brightness is sufficient but the depth of field is small, or brightness is improper although the depth of field is considerable. Consequently, the endoscope needs such light control means that a favorable observation range is ensured and at the same time, brightness remains unchanged.

SUMMARY OF THE INVENTION

It is, therefore, an object of the present invention to provide an endoscope apparatus which uses the AI device in the attachment TV camera for endoscopes, always ensures the brightness of an object image most suitable for photography, and brings about a practical pan-focus state in which a user's operation load is reduced to a minimum.

In order to achieve this object, the endoscope apparatus according to the present invention is equipped with an optical system for forming an object image; a solid-state image sensor for receiving the object image formed by the optical system; illuminating means for irradiating an object with illuminating light; light control means for changing the brightness of the illuminating light; stop means whose aperture is variable disposed in the optical system; detecting means for detecting the brightness of the object image; and control means for controlling the stop means and the light control means so that an intensity of a signal output from the solid-state image sensor is kept nearly constant in accordance with brightness information derived from the detecting means.

Specifically, the endoscope apparatus of the present invention is constructed so that where the brightness of the brightness information obtained from the solid-state image sensor exceeds a predetermined brightness, the aperture of the stop means is diminished in preference to others, while where the brightness of the brightness information is below the predetermined brightness, the amount of light of the light source device can be increased by priority. After the aperture of the stop means has been minimized, the light source device is driven, and after the amount of light of the light source device has been maximized, the stop means is operated.

Further, the endoscope apparatus of the present invention includes an optical system for forming an object image; a solid-state image sensor for receiving the object image formed by the optical system; illuminating means for irradiating an object with illuminating light; detecting means for detecting the brightness of the object image; and driving means for changing an optical path length between the optical system and the solid-state image sensor in accordance with brightness information derived from the detecting means.

This and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, it will be expedient to explain the function of the present invention. In FIG. 3, the position of a point e on the luminance curve B of the light source indicates that where the luminance Bk of the light source is fixed like the curve B, the aperture of the stop of the AI device becomes $\phi 1$, as in the prior art, when the favorable image illuminance E' is acquired at the distance x1 from the distal end portion of the endoscope to the object. Consider the image illuminance E' to be made constant at the illuminance E'1 by operating only the AI device from this situation. Points d and g indicate the positions where the aperture of the stop has been change to be E'=E'1 on the luminance curves A and C of the light source shown in FIG. 2. Corresponding apertures $\phi 2$ and $\phi 3$, in terms of the aperture $\phi 1$, become $\phi 2 < \phi 1 < \phi 3$.

Figure 4:
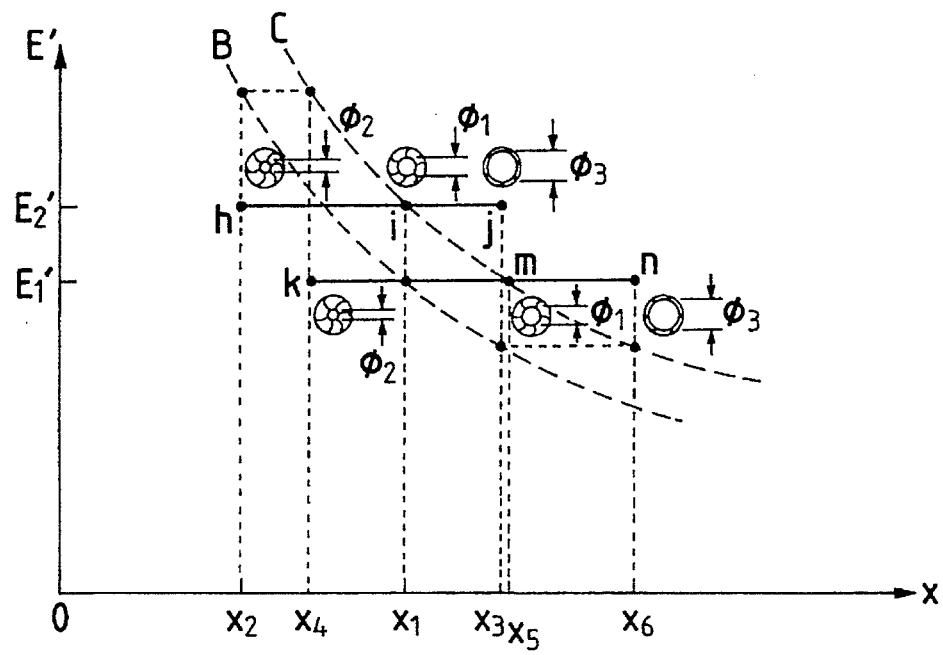
FIGS. 4 and 5 are diagrams each showing the relationship between the object distance and the image illuminance where the luminance of the light source is changed in the endoscope apparatus of the present invention.

A point i on the luminance curve C of the light source shown in FIG. 4 indicates that the aperture of the stop of the AI device is made constant as $\phi 1$ and at the same time, the source stop (light control means) of the light source device is operated to change the luminance Bk of the light source from the curve B to the curve C, so that the image illuminance changes from E'1 to E'2. Here, E'1<E'2.

In this way, the points d, e, and g shown in FIG. 3 change to points h, i, and j in FIG. 4, respectively. Since this situation is better than favorable brightness, the distance x from the distal end portion of the endoscope to the object is increased in order to obtain the favorable image illuminance E'1. In this case, the limit of the distance x corresponding to E'=E'1 changes from the state of x2<x<x3 relative to the points d to g to the state of x4<x<x6 relative to the points k to n.

Figure 5:
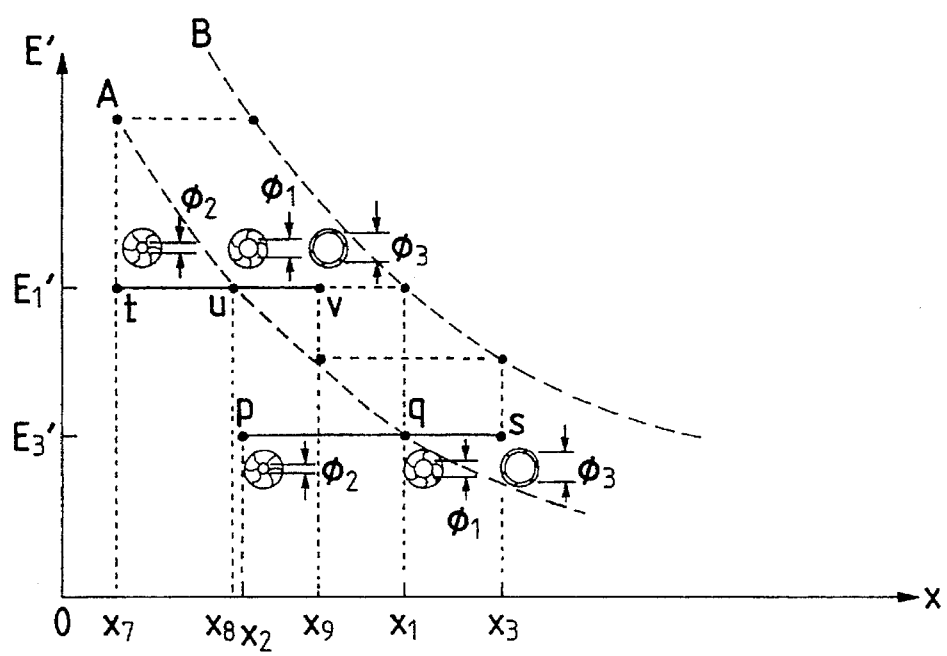

This distance is found as that corresponding to a point on the luminance curve C such that the distances x2 and x3 regarding the luminance curve B are equivalent in the image illuminance E'. Similarly, as shown in FIG. 5, when the state of the luminance of the light source is changed from the curve B to the curve A, the points d, e, and g depicted in FIG. 3 change to points p, q, and s in FIG. 5, respectively. The image illuminance E' thus changes from E'1 to E'3. In order to make this state equivalent to the image illuminance E'1, it is only necessary to define the distance x as x7<x<x9 corresponding to points t to v.

Figure 2:
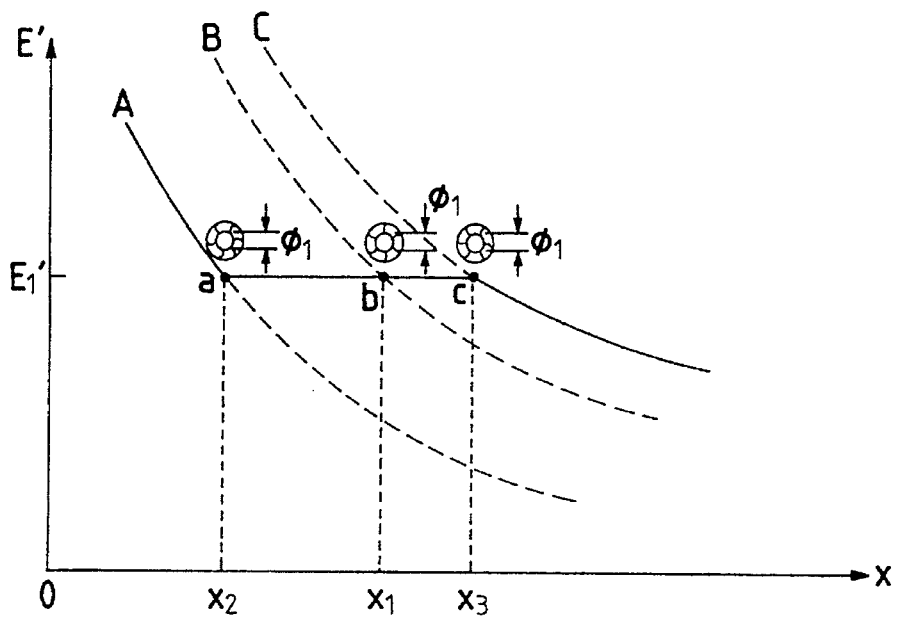
FIG. 2 is a diagram showing the relationship between the object distance and the image illuminance where the luminance of a light source is changed in FIG. 1.
Figure 3:
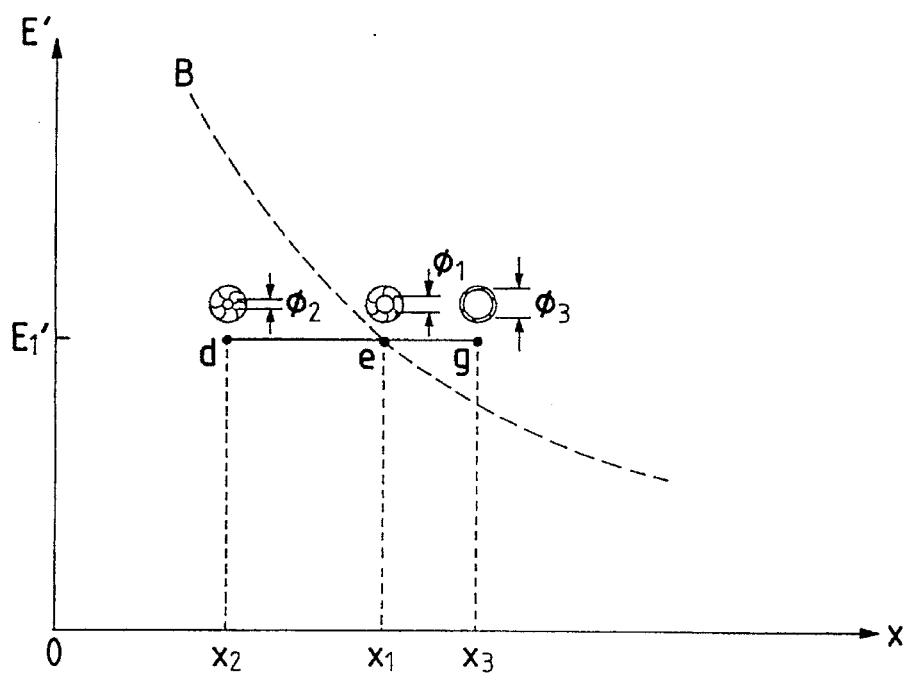
FIG. 3 is a diagram showing the relationship between the object distance and the image illuminance where the luminance of the light source is fixed in the endoscope apparatus according to the present invention.

When FIGS. 3 to 5 are discussed as a whole, the state where the stop has the aperture $\phi 1$ is the same as that shown in FIG. 2, and thus the range of the point u in FIG. 5 to the point m in FIG. 4 corresponds to that of the points a to c in FIG. 2. Consequently, the range is extended in which the illuminance of the image can be held to E'1 (constant) corresponding to the variable aperture of the stop. This extension is in the ranges of the points m to n in FIG. 4 and the points t to u in FIG. 5.

If, however, both the aperture of the stop and the brightness of the light source are variable, various settings can be made by combining the aperture of the stop with the brightness of the light source even in the case of the same image illuminance E'. For example, according to the luminance curve C of the light source shown in FIG. 4, the aperture of the stop is stopped down to a minimum at the object distance x4 (the point k), while for the luminance curve A of the light source shown in FIG. 5, the distance x4 lies between the points u and v, and the aperture of the stop is considerably wide open. Hence, proper control over the aperture of the stop and the brightness of the light source makes it possible to provide such illumination as to fulfil the requirements of both the brightness and the depth of field.

Referring to FIGS. 3 to 5, in the range in which the illuminance can be kept constant (the range of the points t to n), the points t to k (namely, the object distances x7 to x4) are in the range in which light control becomes possible with the aperture of the stop stopped down to a minimum. Up to here, the aperture of the stop is minimized with the largest possible depth of field at a short distance. At a longer distance (where the object is situated farther away), the light control is made by using the stop because it is necessary to make the aperture of the stop larger. The stop is fully opened at the object distance x6, and at a farther distance, the light control becomes impossible.

Since it is considered to be ideal that the optical system for endoscopes is brought into a pan-focus state, it is desirable that the aperture of the stop is stopped down to a minimum. Thus, in order to fix the image illuminance E' of the CCD, it is only necessary, as indicated by solid lines in FIGS. 6A–6C, that in the state where the aperture of the stop of the AI device is set to a minimum, the amount of light is increased by the light control of the light source, and when the amount of light controlled is maximized, the stop is gradually opened. In other wards, it is only necessary that the stop of the AI device is controlled in preference to the light control of the light source, and when the aperture of the stop is minimized, the light control is exercised over the light source.

Figure 6A:
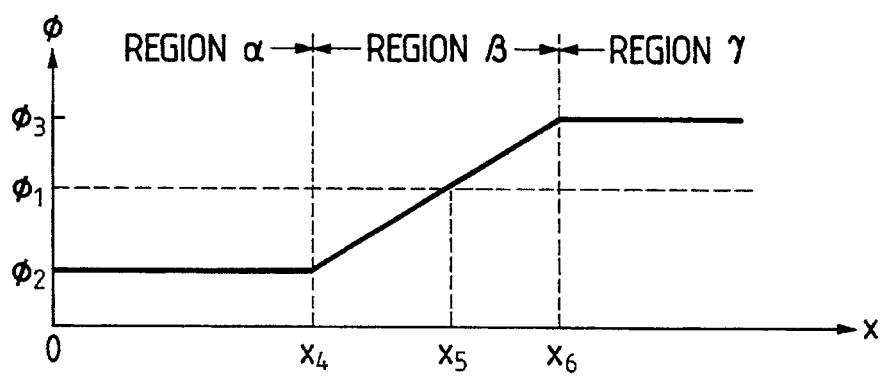
FIGS. 6A, 6B, and 6C are diagrams for explaining the function of the present invention regarding changes of the aperture of a stop, the light control of the light source, and the image illuminance, respectively.
Figure 6B:
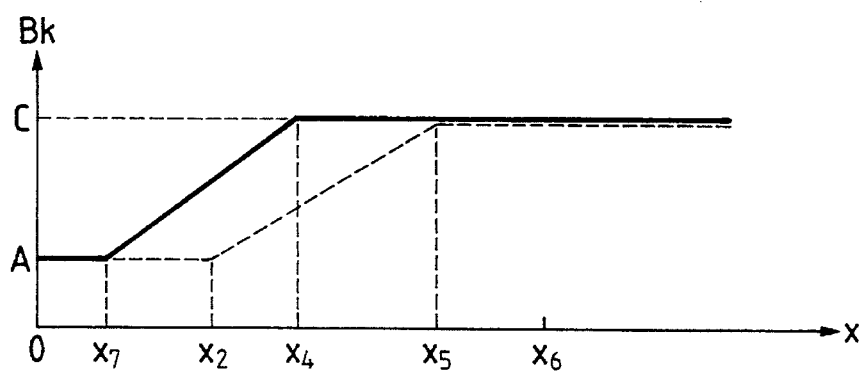
Figure 6C:
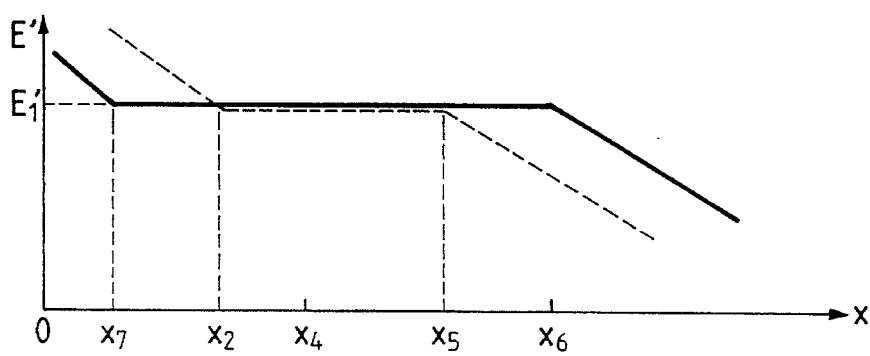

As shown in FIG. 6A, when the object distance x is in the limit of x<x4, the aperture of the stop is stopped down to a minimum ($\phi 2$). Although, as shown in FIG. 6B, the source luminance Bk is minimized up to the distance x7, the image illuminance E', as shown in FIG. 6C, changes with the distance x because the object lies nearby. At the distance x7, the image illuminance E' reaches the desired value E'1. From this point, the source luminance Bk gradually increases up to the distance x4, and thus the illuminance E' can be kept constant with the aperture of the stop minimized. Since the source luminance Bk is maximized at the distance x4, as shown in FIG. 6A, the stop is gradually opened, thereby keeping the image illuminance E' constant. Beyond the distance x6, the object is too far, and the illuminance E' decreases with increasing distance. Broken lines depicted in FIGS. 6A–6C indicate changes in the conventional system illustrated in FIG. 2.

Thus, in FIGS. 6A–6C, compared with the states of the conventional endoscope system drawn by the broken lines, the depth of field is improved and pan-focus design is achieved in accordance with a decrease of the aperture of the stop in the limit of x<x5, where x5 is the distance at which the aperture of the stop reaches φ1. Further, in the limit of x>x5, the depth of field becomes small in accordance with an increase of the aperture of the stop, compared with the conventional apparatus, but the shape of the object has come to be practically discriminated. Thus, in the conventional endoscope apparatus, the corresponding region, although lying in the depth of field, is insufficient in brightness and impossible for observation, whereas in the endoscope apparatus of the present invention, the shape of the object has come to be practically discriminated, and the operation performance of the apparatus is improved accordingly.

Calling φ2 the minimum aperture of the stop, F the focal length of the optical system, and Px a pixel pitch in the horizontal scanning direction of the CCD, it is favorable that the endoscope apparatus of the present invention satisfies the condition:

$$\phi 2 \geq 2.15 \times 10^{-4} F/Px \qquad (2)$$

Figure 7:
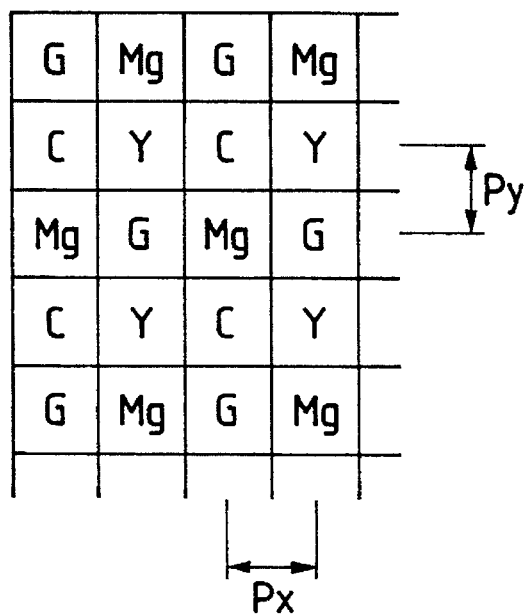
FIG. 7 is a view schematically showing the surface of a solid-state image sensor.

In the endoscope apparatus according to the present invention, when the distance x from the distal end portion of the endoscope to the object is in the limit of x<x4 as shown in FIG. 6A, the aperture of the stop of the AI device is desirable to be fixed at φ2. If, however, the stop is set to such an extremely small aperture, a reduction in resolving power will occur because of a diffraction limit, with the result that the effect of improvement of the depth of field secured by stopping down the stop cannot be achieved. In order to avoid such a problem, it is necessary to define the condition given by Eq. (2) which is optimum for endoscopes. This condition can be found as follows:

The above condition, when the aperture of the stop is made small, is specified in view of the balance between a pan-focus effect by which the depth of field is made large and a reduction in resolving power due to diffraction in the stop. It is assumed that a color filter, such as that shown in FIG. 7, is placed on the surface of the CCD. Individual filter elements of the color filter are provided corresponding to individual pixels which give rise to photoelectric conversion, and are represented by G for green, Ng for magenta, C for cyan, and Y for yellow. Since the CCD reads out two pixels as one unit in a horizontal direction, a Nyquist rate fn is given by $$fn = 1/(2 Px) \qquad (3)$$

In a TV photographic optical system using the CCD, since an optical low-pass filter for eliminating moiré is in general disposed, there is a need to consider the frequency characteristic of the entire optical system, including this filter. Where the Nyquist rate is given by Eq. (3), in view of the use of a TV camera attached to the eyepiece section of the endoscope, the optical low-pass filter disposed in the photographic optical system is desirable to have the frequency characteristic such as that shown in FIG. 8. In this figure, the axis of abscissas is a spatial frequency f (unit: line/mm) and the axis of ordinates is a spatial frequency response represented by MTF (modulation transfer function). A solid curve J represents the spatial frequency characteristic of the optical low-pass filter, and a broken curve K represents the frequency characteristic of the optical system excluding the optical low-pass filter. Although the optical low-pass filter has the characteristic that the response becomes zero on the somewhat low frequency side of the Nyquist frequency fn, a spatial frequency fn' at which the MTF is at least 30%, in terms of the Nyquist frequency fn of the CCD, becomes $$fn' \approx 0.6 fn \qquad (4)$$

This frequency is an effective resolution limit of the CCD.

In contrast to this, the frequency response of the optical system excluding the filter varies with the aperture of the stop, and a diffraction limit (Raleigh's limit) frequency Ca with the optical system is given by $$fa = 1/(1.22 \lambda FNo) = 1395 \phi/F \qquad (5)$$

where λ=587.56 nm, FNO=F/φ, and φ is the aperture of the stop.

Here, although it is required that the aperture of the stop corresponding to the F-number is actually calculated with an effective F-number, a general diopter a non-flexible endoscope is about −1 (m$^{-1}$), and therefore, the object distance regarding the photographic optical system is in the neighborhood of 1000 mm. Since the focal length F of the TV photographic optical system for endoscopes is nearly 10–50 mm, the object distance may be considered to be practically infinite, and the effective F-number may be regarded as about equal to the F-number.

Figure 8:
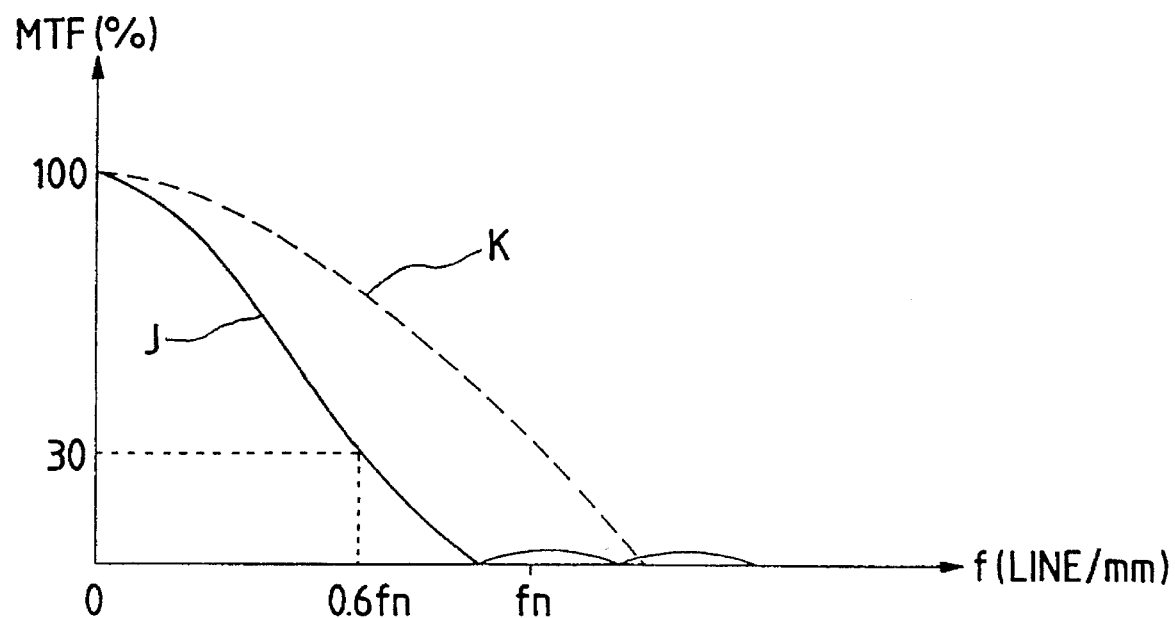
FIG. 8 is a diagram showing frequency characteristics relative to an optical low-pass filter.

The diffraction limit frequency becomes low as the aperture of the stop is diminished, and the broken curve K shown in FIG. 8 is moved to the left of the figure. Subsequently, when the broken curve K is shifted to the left of the solid curve J, the blurring of the image caused by diffraction becomes prominent. In order to obviate this blurring, it is desirable to satisfy the condition:

$$fn \leq fa \qquad (6)$$

The substitution of Eqs. (3) and (5) in Eq. (6) gives the condition of Eq. (2). If the value of the aperture φ2 is below the lower limit of Eq. (2), the degradation of the resolving power will be produced by the influence of diffraction as mentioned above, and the effect of improvement of the depth of field secured by stopping down the stop will not be achieved.

According to the endoscope apparatus of the present invention, as stated above, the use of the AI device in the attachment TV camera for endoscopes makes it possible to always ensure the optimum brightness of the object image, to bring about a practical pan-focus state in which a user's operation load is reduced to a minimum, and to fully utilize the effect of stopping down the stop, without producing the degradation of the resolving power by the diffraction limit.

In accordance with the embodiments shown, the present invention will be explained in detail below.

Figure 1:
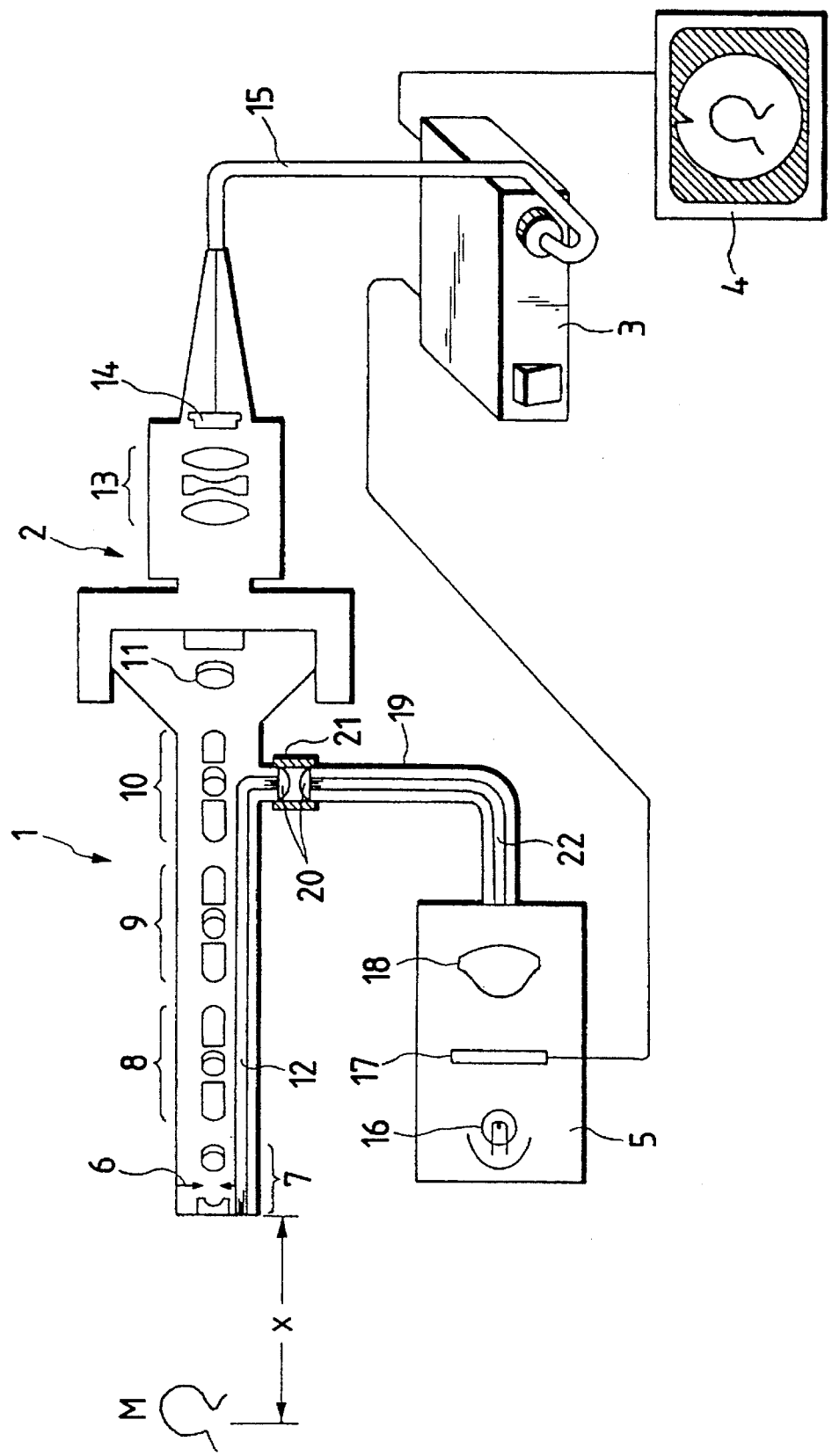
FIG. 1 is a view showing the entire construction of a conventional endoscope apparatus.
Figure 9:
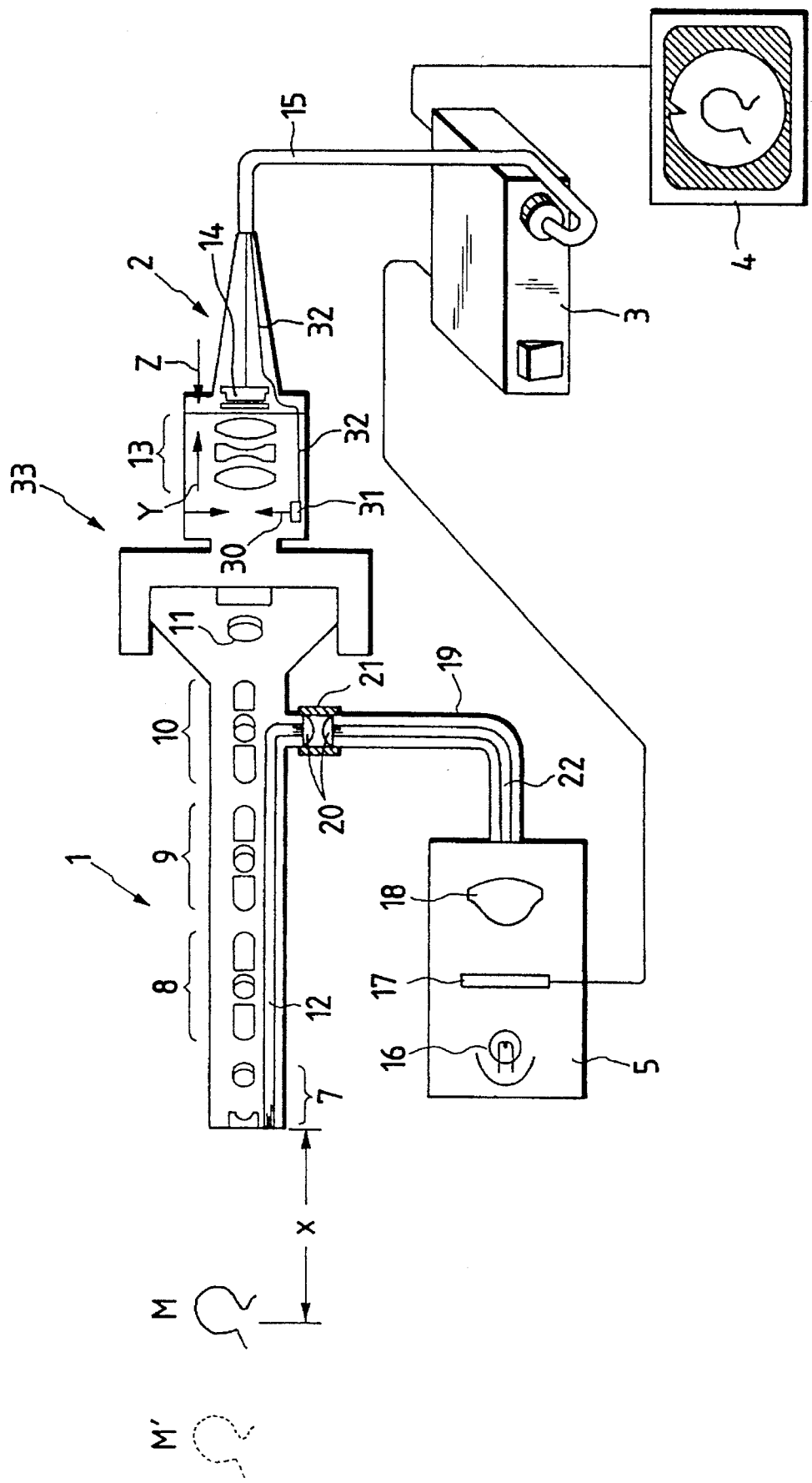
FIG. 9 is a view showing the entire construction of the endoscope apparatus according to the present invention.

FIG. 9 shows the entire construction of the endoscope apparatus according to the present invention. It is the same as that of the conventional apparatus shown in FIG. 1 with the exception that the endoscope 1 and the TV camera head 2 are connected by an optical adapter 33 which includes the adapter lens 13; an auto-iris (stop means: a stop with variable aperture) 30; driving means (such as a motor) 31 for driving the auto-iris 30; and a signal line 32 for supplying a control signal to the driving means 31. The arrangement is such that when the TV camera head 2 is attached to the eyepiece section of the endoscope 1, the position of the auto-iris 30 is in substantial agreement with that of the exit pupil of the eyepiece 11. Here, "substantial agreement" means that deviation is tolerated to the extent that the eclipse of a beam of light due to the auto-iris offers no problem.

Figure 10:
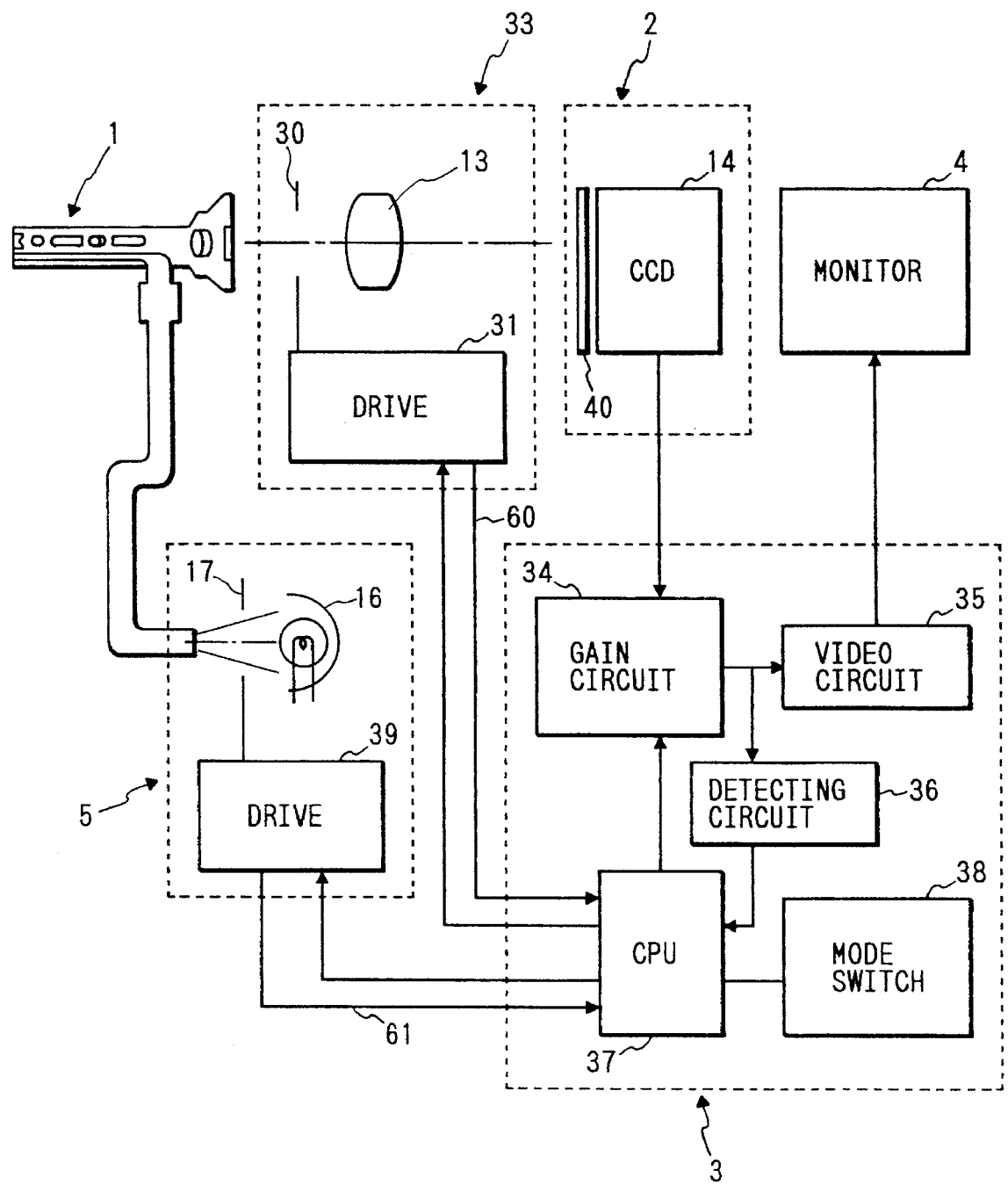
FIG. 10 is a block diagram showing the circuit configuration of the endoscope apparatus in FIG. 9.

Referring now to FIG. 10, the circuit configuration of the apparatus shown in FIG. 9 is described. The endoscope apparatus of the present invention is constructed so that the endoscope 1, the optical adapter 33 having the auto-iris 30 and the adapter lens 13, and the TV camera head 2 having the CCD 14 are removably arranged. The TV camera head 2 is constructed so that it is also used in various kinds of endoscopes. If, therefore, the optical adapter 33 is available in several types to be applicable to endoscopes having a variety of properties, the combination of the optical adapter 33 with the TV camera head 2 can be used as a TV camera which can accommodate the various endoscopes.

A plate-like member disposed on the entrance side of the CCD 14 is an optical low-pass filter 40 for eliminating moiré. The CCU 3 is equipped with a gain circuit 34, a video circuit 35, a brightness detecting circuit 36, a central processing unit (CPU) 37, and a mode switch 38.

An output signal transmitted from the CCD 14 is supplied to the gain circuit 34, and after being amplified to a desired level, is fed to the video circuit 35. The video circuit 35 is adapted to convert this signal into a video signal which can be displayed on the monitor 4, and has the function of processing various signals, as occasion demands. Subsequently, the video signal is transmitted from the video circuit 35 to the monitor 4, on which an image is displayed.

Of the output signals from the gain circuit 34, a part is supplied to the brightness detecting circuit 36, in which the brightness of the object image is detected. Further, this detecting signal is supplied to the CPU 37. In order to set a video output to a proper value in accordance with the detecting signal, the CPU 37 sends out a signal for controlling the gain of the gain circuit 34 and signals for controlling the source stop (light control means) 17 in the light source device 5 and the auto-iris 30 in the optical adapter 33 to control these signals. Signals indicating the stopping-down states of the auto-iris 30 and the source stop 17 are fed from the auto-iris driving means 31 and source stop driving means 39 through signal lines 60 and 61, respectively, to the CPU 37.

First Embodiment

Figure 11:
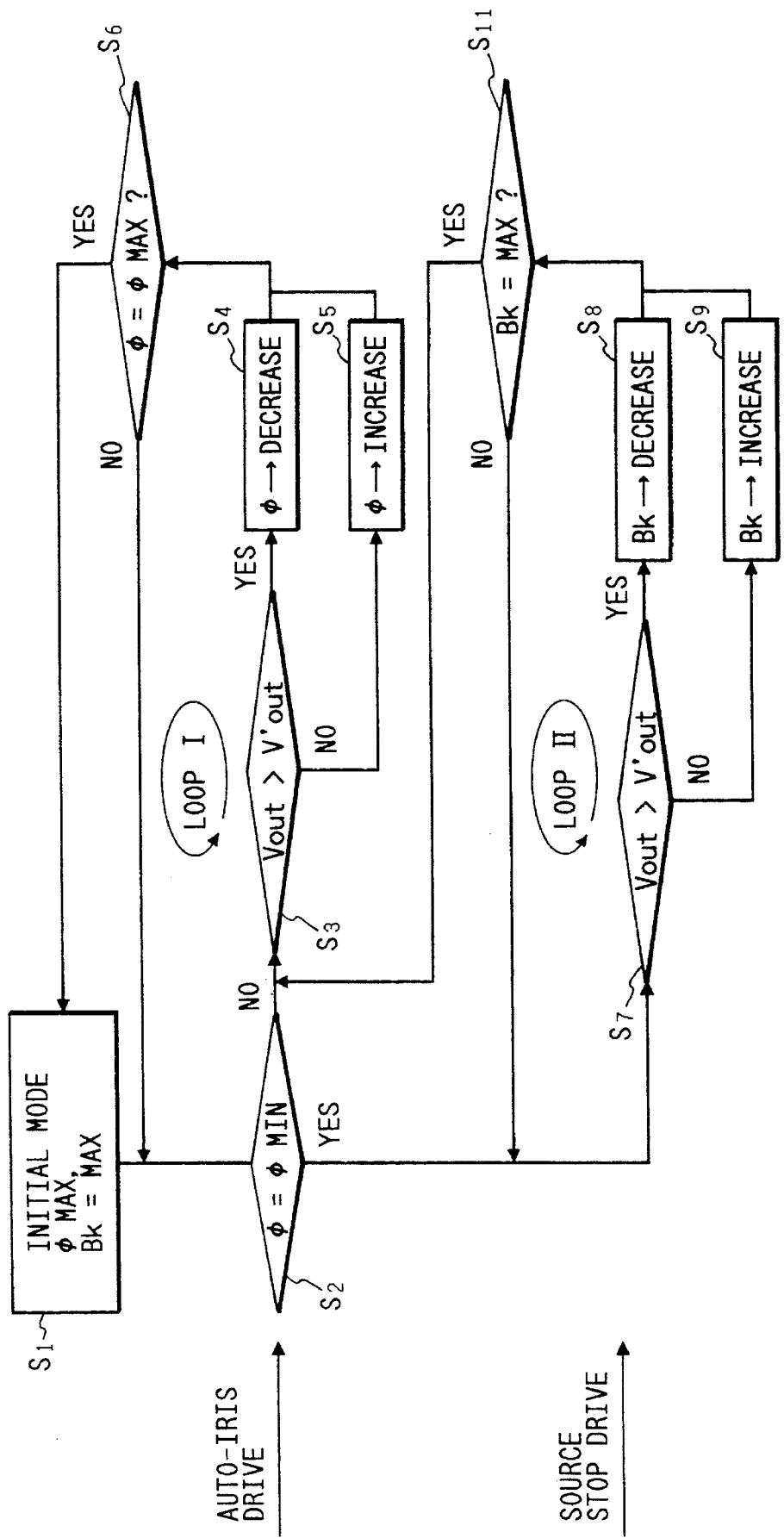
FIG. 11 is a flowchart for explaining the operation of a first embodiment of the endoscope apparatus according to the present invention.

The operation of the first embodiment of the present invention is explained below. FIG. 11 is a flowchart showing the procedure of the light control performed by the CPU 37. This flowchart shows the case where the control starts from the states of a maximum aperture ($\phi$MAX) of the auto-iris 30 and a maximum luminance (Bk=MAX) of the light source. In an initial mode at Step S1, the aperture $\phi$ of the auto-iris 30 in the AI device is maximized [a fully opened state (the state of a region a in FIG. 6A)], and the amount of light of the light source is also maximum. In these states, brightness cannot be further increased, and regions $\alpha$ and $\beta$ shown in FIG. 6A, when observed with this brightness, are too bright and hard to see. Thus, before observations, it is necessary to determine which of the two regions should be used.

At Step S2, unless the aperture $\phi$ is minimum, the AI device is operated in preference to the light source device 5, and Loop I is executed to secure the image illuminance of the region $\beta$ in FIG. 6A. In this case, at Step S3, the aperture of the auto-iris 30 of the AI device is adjusted by comparing the level of a voltage Vout (however, Vout$\propto$E') output from the CCD 14 with that of a reference voltage V'out so that Vout=V'out at Step S4 or S5. The transfer from the region $\beta$ to the region $\gamma$ in FIG. 6A is made, at Step S6, by determining whether the aperture $\phi$ is maximum. If it is maximum, this state will be identical with the initial mode and thus the operation will be returned to Step S1.

More specifically, in Loop I shown in FIG. 11, a determination is made, at Step S2, as to whether the aperture of the auto-iris 30 is minimum. If not, then the region $\beta$ is to be used. In this case, at Step S3, a determination is made as to whether the voltage Vout is higher than the voltage V'out. If so, the output from the CCD 14 will be too high (too bright), and at Step S4, a driving signal is sent from the CPU 37 to the driving circuit 31 to diminish the aperture $\phi$ of the auto-iris 30. If not, by contrast, at Step S5, the aperture $\phi$ of the auto-iris 30 is increased. By driving the driving means 31 of the auto-iris 30, the image illuminance is properly maintained. In this section (Loop I), the region $\beta$ is controlled, that is, control is made so that the aperture of the auto-iris 30 is changed, thereby adjusting the image illuminance.

After the determination at Step S3, if the output is not proper even when the aperture of the auto-iris 30 is reduced, the aperture of the auto-iris 30 will be eventually minimized to affirm the determination at Step and control is now out of Loop I. This situation corresponds to the region $\alpha$ and the aperture of the auto-iris 30 is fixed at a minimum.

Subsequently, after the aperture $\phi$ of the auto-iris 30 has been minimized, the light source device 5 is used with the aperture $\phi$ fixed and Loop II is executed to adjust brightness. Then, the luminance Bk of the light source is controlled so that the level of the voltage Vout is equal to that of the desirable voltage V'out with the aperture $\phi$ fixed. Specifically, at Step S7, a determination is made as to whether the voltage Vout is higher than the voltage V'out. If so, the output remains too high, and at Step S8, the luminance Bk will be adjusted. In the endoscope apparatus of the present invention, the control signal is sent from the CPU 37 to the source stop driving means 39 and the aperture of the source stop 17 is diminished so that the amount of light fed to the light guide cable 19 is decreased. In this way, the image illuminance is properly maintained.

When the aperture of the source stop 17 is maximized as the result of its increase, there is the fear that the adjustment of brightness is not completely made only by the control of the source stop 17. In this instance, Step S11 in Loop II is provided to return the control to Loop I and determine whether the adjustment of the aperture of the auto-iris 30 is needed. The determination of the transfer to the region $\gamma$ is made by the same procedure as in Loop II.

Although in the above description the initial mode at Step S1 is specified as "$\phi$MAX" and "Bk=MAX", it is also possible to enter the control loop from an arbitrary mode. The apparatus of the present invention is intended to secure the object image by the auto-iris 30 of the smallest possible aperture. Hence, where the arbitrary mode is set as the initial mode, it is only necessary to determine the state of the source stop 17 as the first step, set the aperture of the source stop 17 to a maximum, and then perform the control described in connection with FIG. 11.

The electric circuit corresponding to the flowchart mentioned above is the block diagram already shown in FIG. 10. By this circuit configuration, the endoscope apparatus can be realized which always ensures brightness most suitable for endoscopes and which, brings about a pan-focus state that reduces the user's operation load to a minimum. In this case, it is favorable that the minimum aperture of the auto-iris 30 is set by the condition of Eq. (2). Also, although procedures for controlling the amount of light of the light source are available in two kinds, one for changing the luminance by using a filter, such as an ND filter, and the other for changing the numerical aperture (NA), either of them can be used in view of the image illuminance on the CCD.

Second Embodiment

In recent years, electric light control means usually called an electronic shutter has come into prominent use. This embodiment uses the electric light control means for the light control shown in the first embodiment. Reference is now made to the operating conception of the electronic shutter.

Figure 12A:
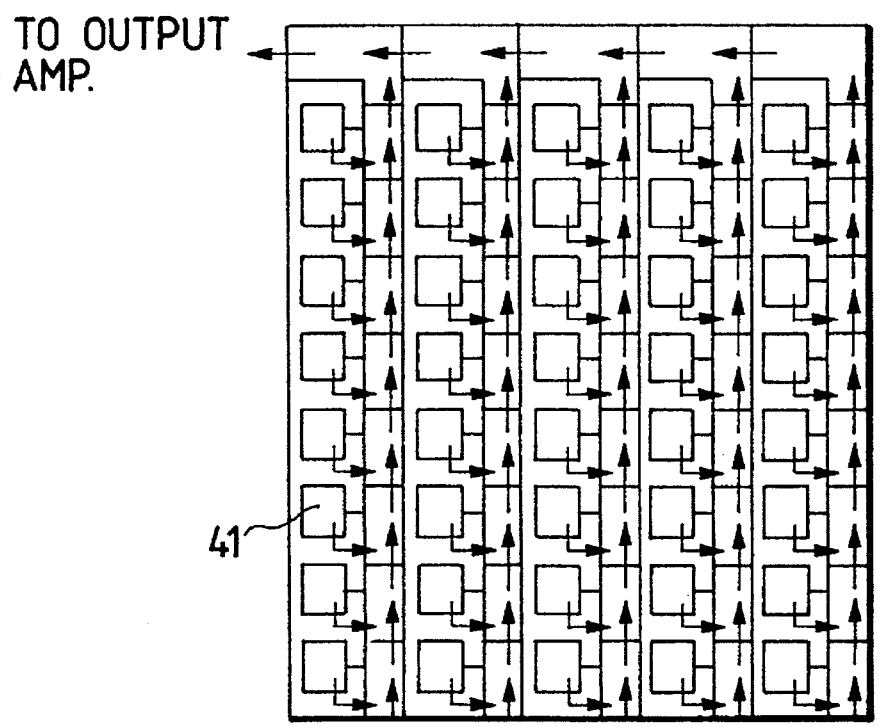
FIGS. 12A and 12B are views schematically showing configurations of the photoelectric conversion surface of the solid-state image sensor of an interline system.
Figure 12B:
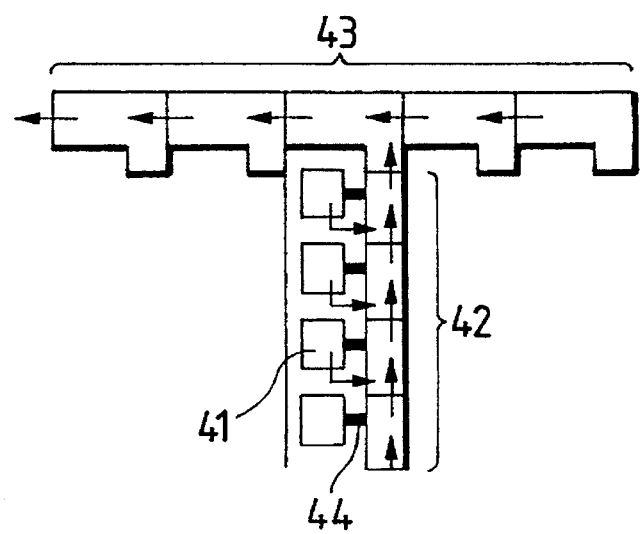

FIGS. 12A and 12B show schematic views of the photoelectric converting surface of the CCD of the interline system. As shown in FIG. 12A, square photodiodes 41 are arrayed longitudinally and laterally, and one array in a lateral (horizontal) direction corresponds to one line. Further, as shown in FIG. 12B, a vertical (V) CCD shift register 42 is disposed, adjacent to each row of the arrayed photodiodes, in a longitudinal direction, and at its output terminal, a horizontal (H) shift register 43 is laterally provided. These shift registers of the CCD are analog shift registers, which are adapted to output electric charges one after another in synchronization with given driving pulses.

In a photodiode section, each of the photodiodes 41 is provided with a charge-storage portion, in which a photoelectric charge generated is stored. A charge transfer gate 44 is disposed between the charge-storage portion and the V CCD shift register 42, and when charge transfer pulses are given at once for one field, all photoelectric charges are simultaneously shifted through the charge transfer gates 44 to the V CCD register 42. Subsequently, whenever vertical driving pulses (V pulses) are given at once for one line, the photoelectric charges are simultaneously passed upward (to the upper portion of the figure) for one line. The H shift register 43 is located at the position where the photoelectric charges are transferred, so that whenever horizontal driving pulses (H pulses) are given, each of the photoelectric charges is passed sideward (to the left of the figure) for one pixel, and after being converted into a voltage signal by an output amplifier, is output. In this way, the information of individual pixels is continuously read out from the top left to the bottom right of the image surface and is output as video signals for one field.

In this case, it is possible to adjust the brightness of the image by controlling the time required for charge storage. For example, an ordinary CCD of the NTSC system stores the electric charges in 1/60 (sec) and transmits the resultant signals to the V CCD register 42. If, however, the time for charge storage is adjusted within the range of 1/60–1/8000 (sec), a proper exposure can be obtained even in the case of a fairly bright image.

The second embodiment uses such an electronic shutter to thereby secure the same effect as in the first embodiment. In FIG. 6B, even where the amount of light of the light source having no automatic light control function is C (=constant), if the time for charge storage is made shorter by the electronic shutter in the range of the distances xT–x4, the illuminance on the image surface can be kept constant similar to the case where the light control means of the light source device is used.

Figure 13:
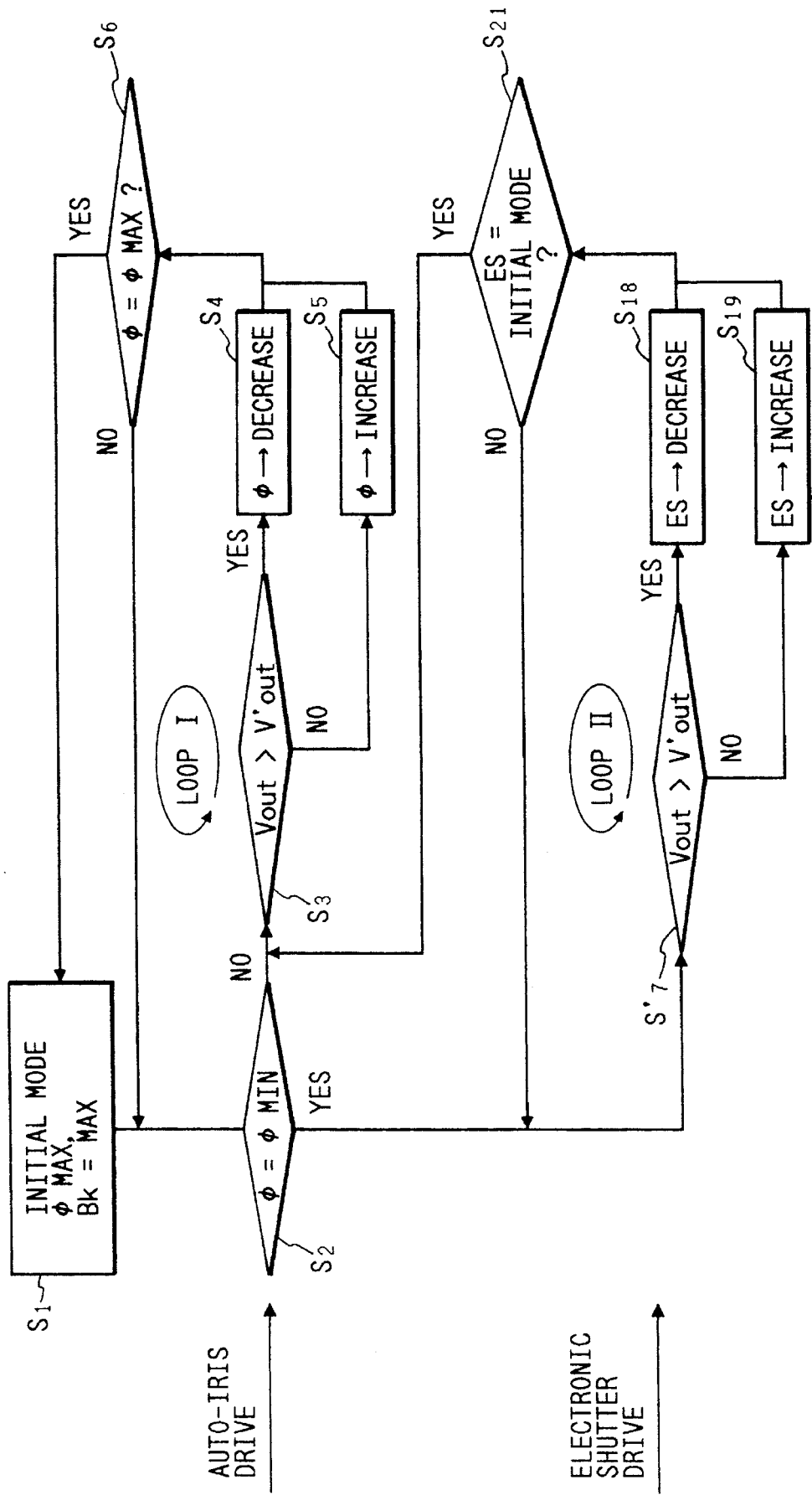
FIG. 13 is a flowchart for explaining the operation of a second embodiment.

FIG. 13 shows a flowchart in the second embodiment. It is the same as that shown in FIG. 11 with the exception that Steps S8 and S9 are replaced by Steps S18 and S19, respectively, and Step S11 is replaced by Step S21. Here, the legend "ES→DECREASE" of Step S18 means that the time for charge storage is decreased by the electronic shutter mechanism, while the legend "ES→INCREASE" of Step S19 means that the time for charge storage is increased. At Step S21, the legend "ES=INITIAL MODE ?" means whether the time for charge storage has been returned to the initial mode, namely, in this instance, whether it is the longest.

In addition to the effect of realizing the endoscope apparatus close to the pan-focus state, the second embodiment can eliminate the circuits of the light source device 5 and the camera control unit 3 from the circuit configuration shown in FIG. 10 because the automatic light control function need not be provided in the light source device. Consequently, the cost reduction of the apparatus is expected. Of course, the combination with the light source device having the automatic light control function brings about the same effect as in the first embodiment. Alternatively, the combination with the light source device having no automatic light control function produces the effect which is little short of a pan-focus state under a proper exposure, independently of the function of the light source, if the apparatus is constructed to secure the effect of the second embodiment. Hence, the endoscope apparatus provides a more favorable system.

Further, as shown in the first and second embodiments, moderate brightness of the image is ensured and the attachment TV camera for endoscopes close to the pan-focus state is realized by adequately operating the auto-iris. In this case, it is also possible to afford an attachment TV camera which is applicable to an autoclaving method (a high-pressure vapor sterilization method), in addition to the effect of reducing the user's operation load. Such an endoscope apparatus is provided with a higher value added for the user. What follows is a detailed description of this apparatus.

The autoclaving method is to sterilize a camera by leaving it placed in an autoclave containing a high-pressure vapor of 135° C. for five minutes, and is known as a sterilization method for medical instruments which is relatively low in running cost. In recent years, attachment cameras for endoscopes have particularly found uses in many surgical operations under endoscopy, and the advent of autoclaving TV cameras is strongly desired. However, autoclaving should be such that cameras have resistance to the repeated performance of sterilization in the high-pressure vapor. Thus, in order to realize the autoclaving camera, the TV camera head 2 shown in FIG. 9 needs a structure to be fully enclosed. However, where such a TV camera head has a movable part for focus adjustment of the camera, it is impossible to form the fully enclosed structure. For example, if an attempt is made to seal a focus knob with an 0 ring, the amount of turning effort will be too large to turn the knob with a user's force. Moreover, after the camera has been autoclaved several hundreds of times, the rubber material of the O ring is deteriorated, and the 0 ring ceases to be useful. Consequently, for the autoclaving camera, it is necessary to construct a pan-focus TV camera head having no focus mechanism.

Third Embodiment

The constructions shown in the first and second embodiments make the realization of the endoscope apparatus little short of a pan-focus state to advance materially. However, the addition of electric light control means, such as the above electronic shutter or an auto-gain control (hereinafter abbreviated to AGC), to the apparatus makes it possible to realize a pan-focus endoscope apparatus which reduces the user's operation load, and therefore an autoclaving TV camera.

In this way, the third embodiment is constructed by combining the light control of the first embodiment with the electronic shutter as the electric light control means. In this embodiment, control is made so that the electric light control means is operated in the case where the image remains bright even when the aperture of the stop means has been minimized and the amount of radiation of the light source device has been reduced to a minimum.

In order to bring the pan-focus state, it is desirable that the limit of x7<x<x6 in FIG. 6C is extended as wide as possible. Here, the limit distance on the near point side of the depth of field at the minimum aperture φ2 of the auto-iris is represented by x10. When the distance x10 is in the limit of x7<x10<x4, a region which is too bright for observation is out of the depth of field on the near point side. Such a region is considered to be not originally used for observation, and thus there is little problem. Actually, however, for example, where the reflectance of the object is extremely high, the region may be too bright for observation even at a considerably great object distance, with the resultant limit of x10<x7. In this case, the construction of the first embodiment is such that since in this region the auto-iris has the minimum aperture and the luminance of the light source device also becomes minimum, further light control is not made and an observable depth of field is determined by brightness only.

However, the third embodiment, using the electronic shutter as the light control means, can keep a constant brightness suitable for observation even in the case of excessive brightness to overcome the difficulty that the region is too bright for observation and to intend the improvement of the depth of field to be observed.

Figure 14:
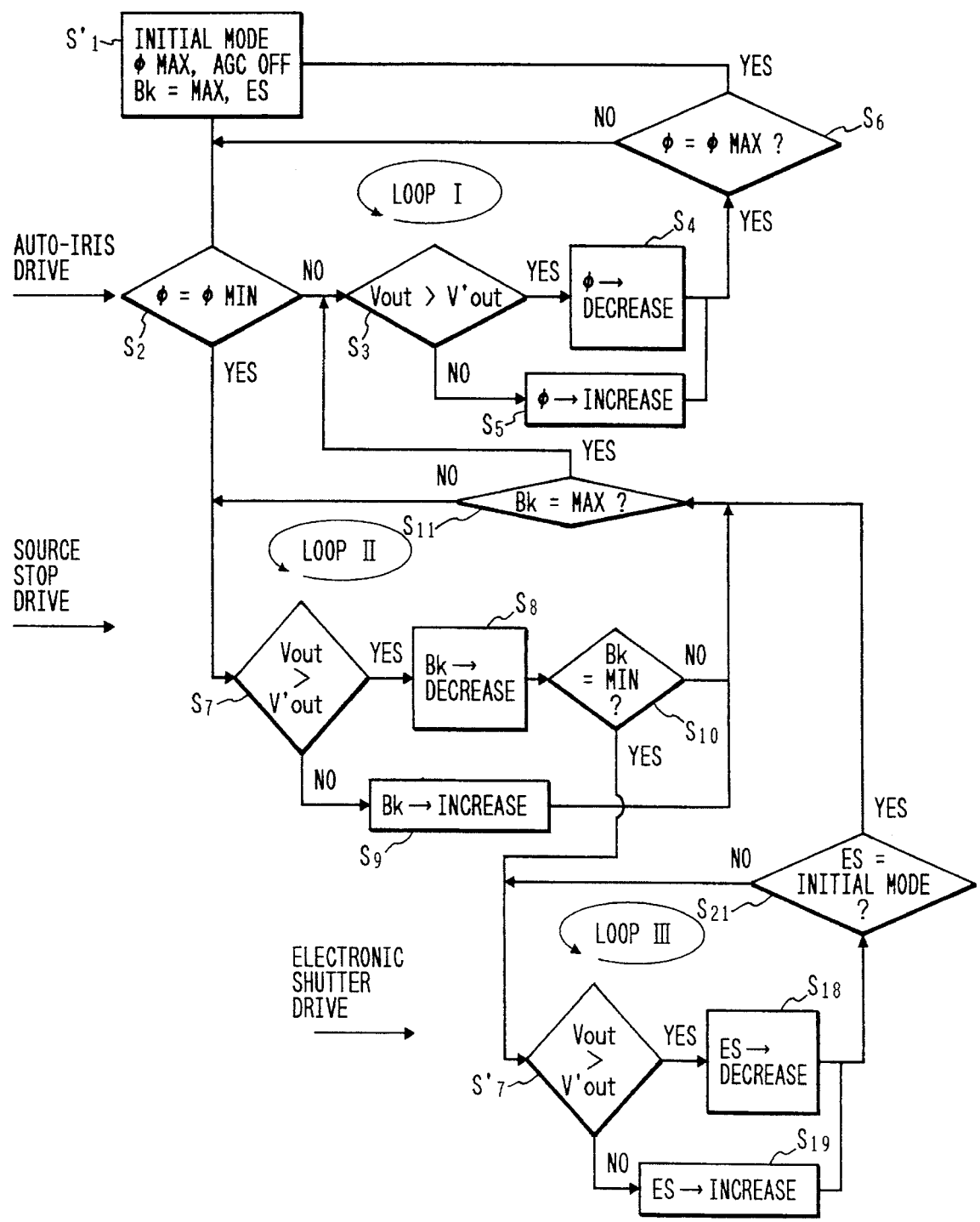
FIG. 14 is a flowchart for explaining the operation of a third embodiment.

FIG. 14 is a flowchart for explaining the operation of the third embodiment. In FIG. 11, when the luminance Bk of the light source is minimized, further control is impossible. In FIG. 14, however, Step S10 is provided between Steps S8 and S11 to determine whether the luminance Bk reaches a minimum value. Control is made in the same manner as in FIG. 11 until the luminance Bk is minimized, but when it has been minimized, the control passes from Loop II to Loop III. Loop III is substantially the same as Loop II shown in FIG. 13, and controls the storage time of the CCD in the states where the aperture of the stop is minimized (Step S2) and the luminance of the light source is minimized (Step S10). Whereby, the electric light control is executed so that a signal obtained from the CCD has an adequate magnitude. Also, the legend "AGC OFF" of the initial mode of Step S'1 indicates the state where an automatic gain control circuit (AGC) which will be described later is not operated.

The conditions under which the electronic shutter is operated, as mentioned above, are that the aperture of the auto-iris is minimum, the amount of light by the automatic light control of the light source device is also minimum, and the output signal from the CCD is beyond moderate brightness. The third embodiment is designed so that when these conditions are satisfied, a routine is entered for driving the electronic shutter. In Loop III, the brightness of the image is adjusted by using only the electronic shutter under the conditions that the luminance Bk of the light source device is minimized and the aperture φ of the auto-iris is also minimized. Where the conditions are violated and brightness changes to have a tendency to darkness, the shutter speed (hereinafter referred to as ES) of the electronic shutter is made to approach the initial mode, and only when the image remains dark even in the initial mode, Loop II is executed to maintain a constant brightness. This is because if control is restored to the loops of the first embodiment with the electronic shutter operated, the auto-iris will be operated under the condition which is disadvantageous to brightness, and thus design is made so that after the electronic shutter has been returned to the initial mode, control is restored to the loops of the first embodiment.

Also, the legend "INITIAL MODE" at Step S21 shown in FIG. 13 indicates that the ES is 1/60 (sec) as a standard, for example, in the CCD of the NTSC system. If a CCD with considerable brightness is available, it may well be set at 1/125 (sec). Further, it may also be set at 1/30 (sec) when brightness is taken into account in particular. Where brightness is adjusted, the ES may be changed by the on-off system or in a multistep manner.

As mentioned above, the third embodiment is constructed with the endoscope apparatus which can be properly operated by combining the light control device of the light source with the electronic shutter as well as with the auto-iris, and hence has a great effect on the improvement of the depth of field to be observed on the near point side.

Fourth Embodiment

First, reference is made to the conception of the operation of the AGC. The signal output from the CCD, after sample-holding and smoothing, is amplified by the amplifier. The brightness of the image can also be adjusted in accordance with the setting of a gain (amplification degree) in this case. The circuit for brightness adjustment by the gain is called the AGC. This adjustment is made by electrically amplifying the output signal from the CCD, and thus if its amplification factor is raised to excess, an electric noise will also be amplified. Conversely, if the amplification factor is excessively lowered, the signal will be liable to saturation. In either case, such adjustment is unfavorable. As such, it is desired that the amplification factor is adjusted to a compromise between both excessive values to obtain moderate image brightness and exposure.

Thus, the fourth embodiment is constructed by combining the light control of the first embodiment with the AGC as the electric light control means. In this embodiment, control is made so that the electric light control means is operated in the case where the image remains dark even when the aperture of the stop means has been maximized and the amount of radiation of the light source device has also been maximized.

Here, the limit distance on the far point side of the depth of field at the aperture φ3 of the auto-iris is represented by x11. When the limit distance x11 is defined as x11<x6 compared with the limit distance x6 on the far point side of the depth of field depending on brightness, the image of an object situated farther than the distance x11 is somewhat blurred because the object is out of the depth of field. If, however, brightness is adequate, the locations of organs in the human body can roughly be confirmed even though clear observations are not made, and a rough orientation of the distal end portion of the endoscope is easily determined. Hence, it is desirable to use brightness suitable for observation as far as possible even at object distance greater than the distance x11. In other words, it is favorable that the limit distance x6 for brightness is great, irrespective of the value of the distance x11. For this purpose, the fourth embodiment uses the AGC for observations of regions farther than the distance x6 in which darkness makes observations difficult.

Figure 15:
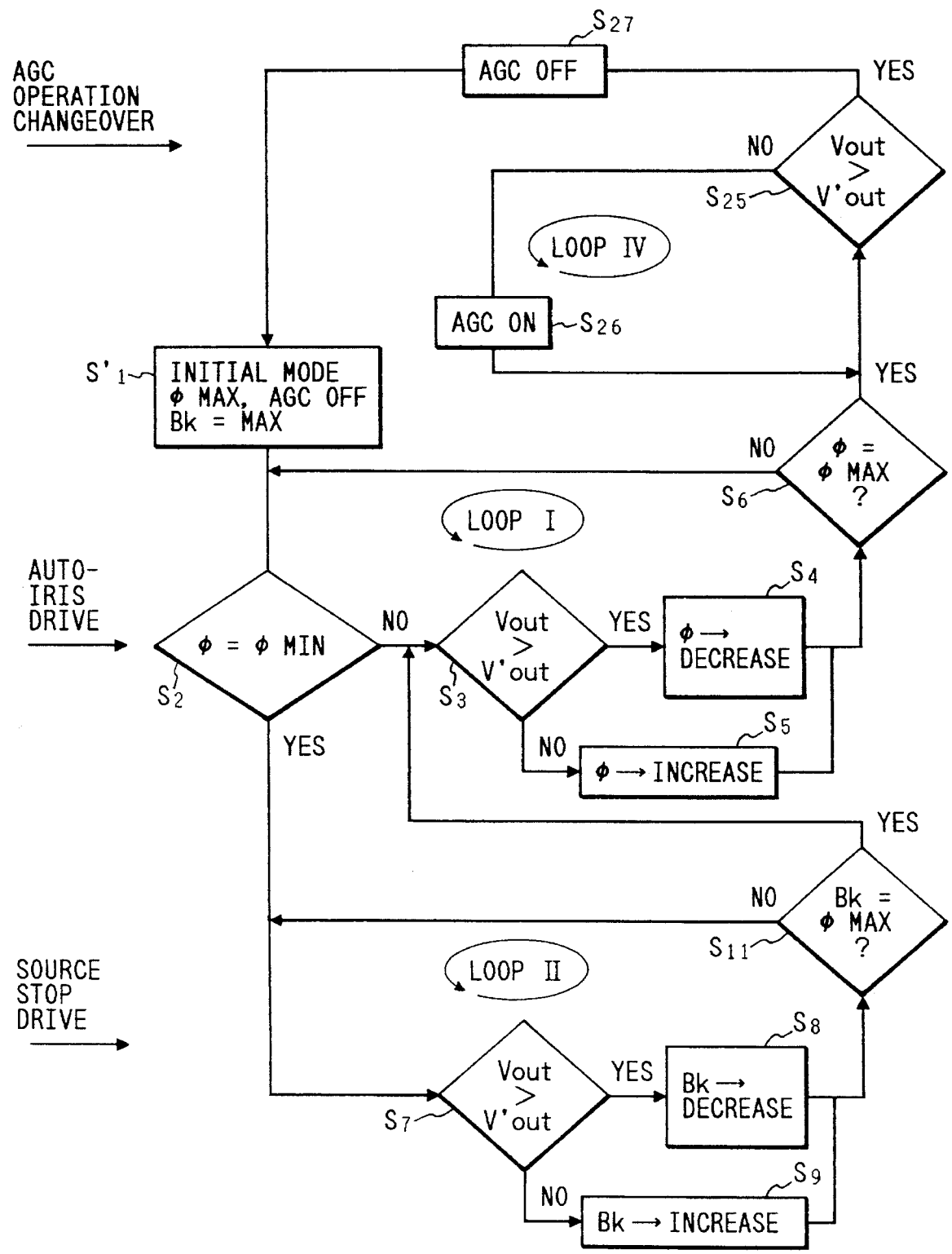
FIG. 15 is a flowchart for explaining the operation of a fourth embodiment.

A flowchart in this case is shown in FIG. 15. The fourth embodiment is provided with Loop IV for AGC operation control on the way back from the branch of Step S6 of the flowchart shown in FIG. 11 to the initial mode. The operating conditions of the electronic shutter, as mentioned above, are that the aperture of the auto-iris is maximum, the amount of light by the automatic light control is increased to a maximum, and the output signal from the CCD has a value lower than proper brightness. When these conditions are satisfied, the AGC turns to an on state. In this embodiment, it is desirable that an AGC circuit is disposed behind the brightness detecting circuit. For example, where the circuit shown in FIG. 10 is used, it is desirable that the AGC circuit is situated inside the video circuit 85. With such a configuration, the determinations of Steps S26 and S27 (namely, the determination at Step S25) will be made by the output signal from the CCD. Consequently, even though apparent brightness on the TV monitor varies, the standard of this brightness need not be changed and a simple circuit configuration can be realized. It is for this reason that if the determination of Step S25 is made with the intensity of the output signal sent to the TV monitor, the standard will be changed by the operation of the AGC, and standards for determination corresponding to possible states must be previously provided, with a resultant complicated circuit configuration. In this case, if the AGC need not be operated, it will be set to an off state at Step S27 to return to the initial mode and restored to the loop of the first embodiment. The fourth embodiment, constructed in this manner, prevents the AGC which is in an operation state from being restored to the loop of the first embodiment, and the auto-iris from being operated under the condition that is disadvantageous for an S/N ratio.

In the flowchart shown in FIG. 15, the operation of the AGC is considered only under on and off states. If, however, the AGC is designed so that it can be switched in a multistep manner, finer light control can be made while the effect of the fourth embodiment is maintained. Furthermore, even if the time for charge storage of the CCD is set at 1/30 (sec), a slight flicker will be produced, but the effect which is equivalent to that of the AGC circuit can be secured since the image is twice as bright.

According to the fourth embodiment, as stated above, control is made so that the improvement of an electric sensitivity as well as the light control device of the light source and the auto-iris is intended to secure the proper exposure automatically. As such, the depth of field to be observed on the far point side can be improved.

Fifth Embodiment

Figure 16:
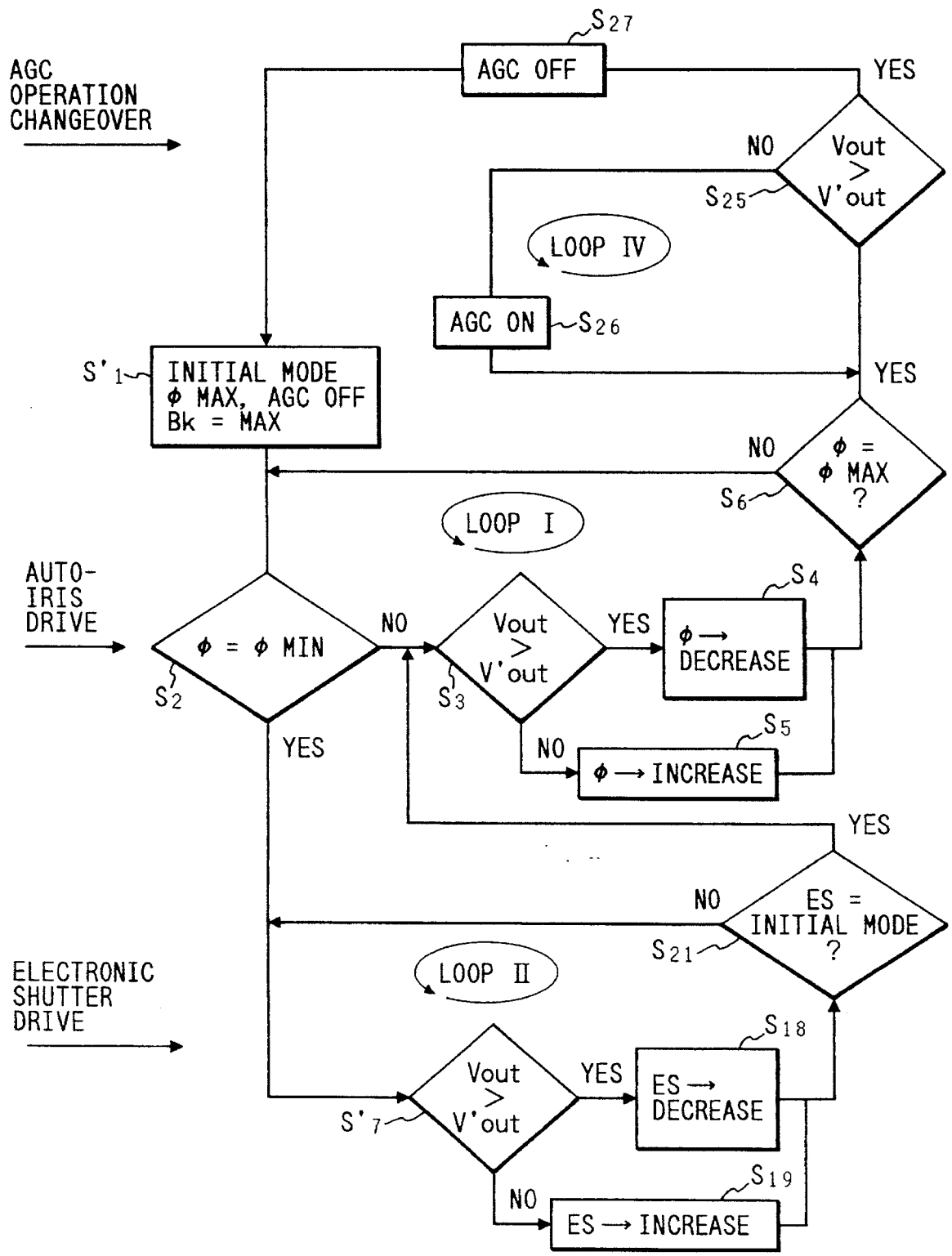
FIG. 16 is a flowchart for explaining the operation of a fifth embodiment.

This embodiment combines the light control shown in the second embodiment with the AGC, and is designed for circuit compactness by the absence of the automatic light control device of the light source and for a reduction in cost of the apparatus. FIG. 16 is a flowchart for explaining the operation of the fifth embodiment.

Sixth Embodiment

This embodiment has the same construction as that shown in the fourth embodiment, but is designed so that the user can adjust brightness directly without automatically operating the AGC mechanism. This is, as described in the fourth embodiment, because the essential purpose of operating the AGC is only to increase a gain so as to secure the maximum brightness within the tolerance of an S/N ratio when observations are made at a great distance, and hence it is only necessary to make a gain adjustment in two steps of the on and off states. In this way, the circuit for automatically controlling the AGC is eliminated, and thereby the simplification and cost reduction of the apparatus can be brought about.

Also, a flowchart in this case, which combines the light control shown in FIG. 11 with the on-off system of an independent AGC, is omitted.

Seventh Embodiment

This embodiment is constructed by a combination of the third and sixth embodiments. It has the feature that the advantages of these embodiments are combined to bring about a great effect of increasing the depth of field on the far point side as well as on the near point side. A flowchart in this case is omitted because it combines the light control shown in FIG. 14 with the on-off control means of an independent AGC.

Eighth Embodiment

This embodiment is constructed by a combination of the third and fourth embodiments. Its feature, like the seventh embodiment, lies in the fact that a great effect is secured that the depth of field is increased on the far point side as well as on the near point side, and a good image quality in this depth of field is automatically provided in every case. The flowchart of the eighth embodiment is omitted because it combines those shown in FIGS. 14 and 15.

In any of the third to eighth embodiments, as mentioned above, the light control means is controlled to be in the optimum order of operation in combination with each electric light control means, as well as the determination of the priority order relative to the operations of the light control device of the light source and the auto-iris. It is, therefore, possible to realize a pan-focus attachment camera for endoscopes in which its observable range is wide compared with those of the first and second embodiments. In this way, an optical system can be realized which is suitable for the attachment TV camera such that not only is the user's operation load reduced, but the autoclave can be used.

Besides each electric light control means mentioned above, it is also quite possible that an ND filter whose transmittance varies with the angle of rotation is inserted and disposed in the optical path from the last surface of the lens 13 of the optical adapter 33 to the CCD 14 shown in FIG. 9, and is rotated in response to the output signal from the CCD 14 or the auto-iris driving voltage to control the brightness of the image. Of course, such a construction also has the same effect as in the third to eighth embodiments, and can be regarded as a type of electric light control means.

Ninth Embodiment

Since the regions β and γ in FIG. 6A are such that brightness is adjusted by the auto-iris 30 and the aperture φ of the auto-iris 30 is approximately maximized, a distant object can be brightly observed, but there is the problem of decreasing the depth of field. If in such regions the adapter lens 13 or the CCD 14 is moved along the optical axis to focus near a far point, an autofocus device can be secured which responds correctly to the position for observation the user requires, compared with an ordinary autofocus device for cameras. For example, in FIG. 9 illustrating the construction of the endoscope apparatus of the present invention, when a distant object M' is photographed, the image position is shifted toward the object, and thus it is necessary to move the adapter lens 13 toward the image (in the direction of an arrow indicated by Y in the figure), or the CCD 14 toward the object (in the direction of an arrow indicated by Z) for focus adjustment. The ninth embodiment, however, is designed so that the focus adjustment is electrically performed and the focus position changes with brightness.

Figure 17:
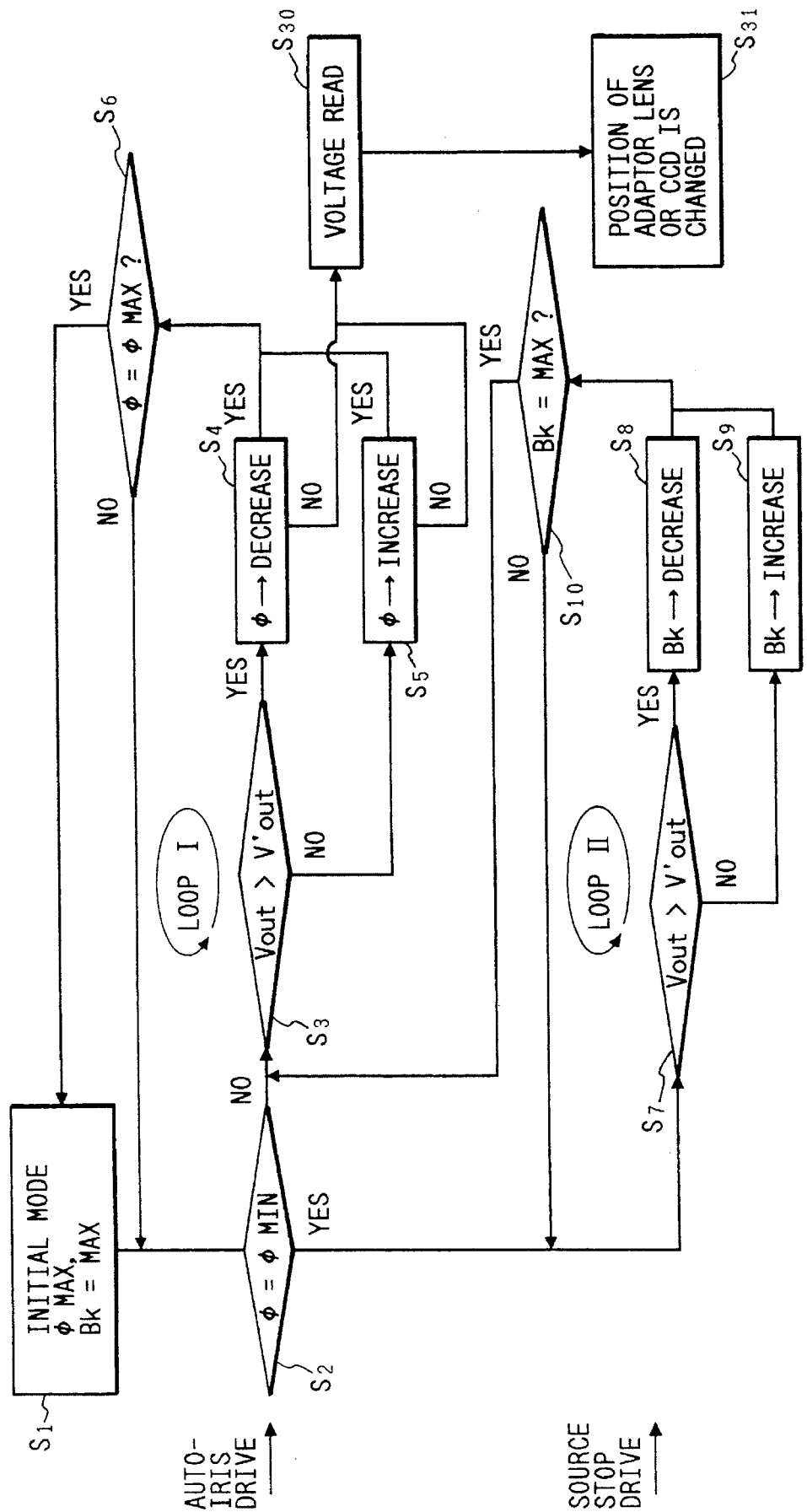
FIG. 17 is a flowchart for explaining the operation of a ninth embodiment.

Specifically, it is merely necessary to previously tabulate and store positions for focus adjustment and to set the position of focus adjustment near the far point in accordance with the aperture of the auto-iris 30 of the AI device. Such a construction can be realized as follows: The signal where the aperture φ of the auto-iris 30 has changed, as shown in the flowchart of FIG. 17, is separated and supplied to a loop for driving the autofocus device, besides Loop I for controlling brightness, so that, at Step S30, a voltage value is read out which corresponds to the appropriate aperture φ of the auto-iris 30 and, at Step S31, the driving device of the adapter lens 13 or the CCD 14 is controlled under the optimum condition in accordance with the voltage value. That is, when the aperture of the auto-iris 30 approaches a fully opened state, control is made so that the adapter lens 13 or the CCD 14 is moved to bring the distant object to a focus.

Tenth Embodiment

Figure 18:
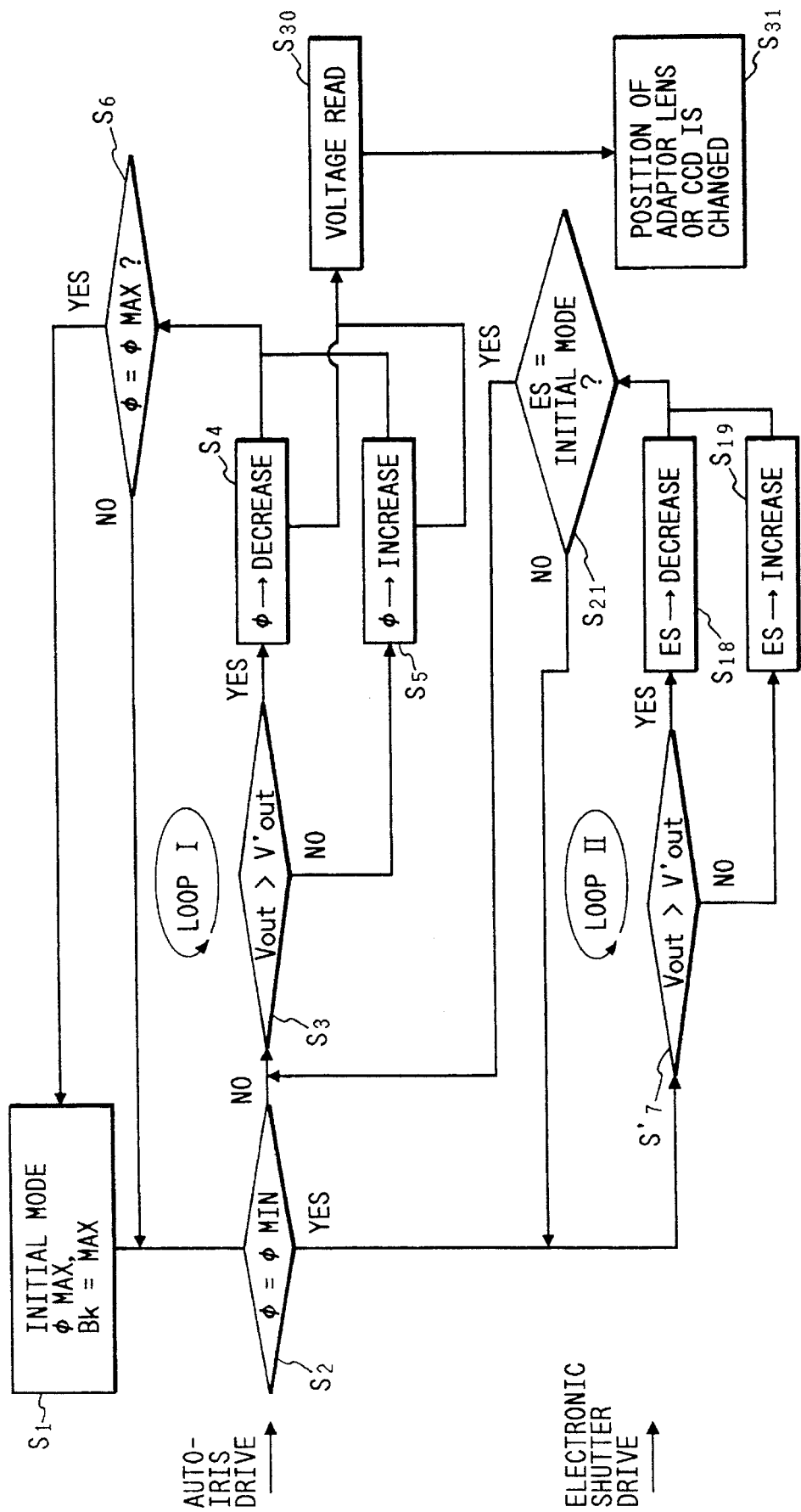
FIG. 18 is a flowchart for explaining the operation of a tenth embodiment.

This embodiment is constructed by using the electronic shutter as the automatic light control means shown in the ninth embodiment. By this construction, the tenth embodiment brings about the same effect as in the ninth embodiment without having the light control circuit of the light source device like the second embodiment. A flowchart for explaining the control procedure in this case is shown in FIG. 18.

Eleventh Embodiment

Figure 19A:
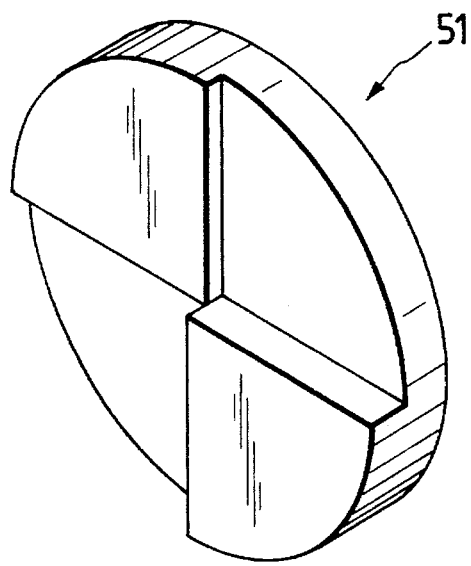
FIGS. 19A and 19B are views showing a filter and the construction of an endoscope adapter section in which the filter is disposed, respectively, in an eleventh embodiment.
Figure 19B:
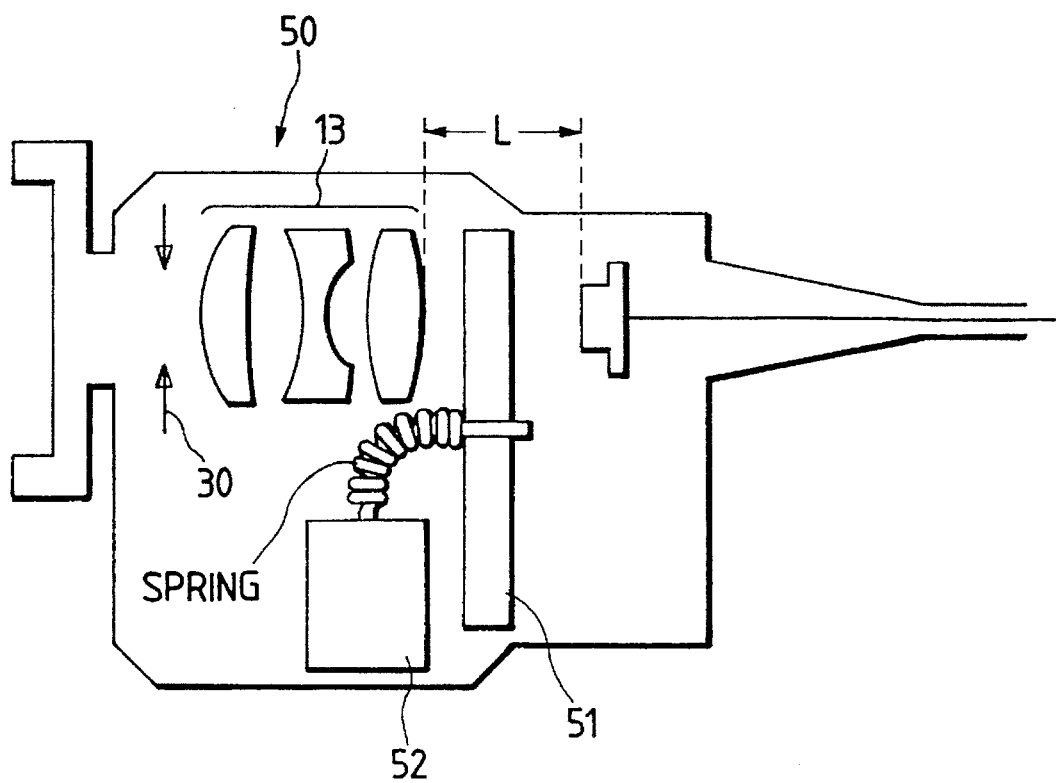

This embodiment carries out the improvement of the focus adjusting procedure shown in the ninth embodiment. In the ninth embodiment, as mentioned above, feedback control is made based on the signal output from the auto-iris or the CCD, and the lens or the CCD is moved along the optical axis for focus adjustment. In the eleventh embodiment, by contrast, an optical element capable of changing an optical path length without altering an actual dimension is inserted in, or removed from, the optical path from the last surface of the lens to the CCD, thereby performing the focus adjustment. For example, as shown in FIG. 19A, a disk-like filter 15 is constructed with fan-shaped glass elements having a refractive index of 1.51663 and thicknesses of 0.8, 2, and 3.2 mm (actual dimensions), and is designed, as shown in FIG. 19B, so that its angle of rotation can be changed in the optical path of an optical adapter 50 by a motor 52. In this way, a flange back length L can be converted to be 14.2, 15, or 15.8 mm (the optical path length).

If the focal length F of the optical system of the TV camera attached to the eyepiece section of the endoscope is set at 20 mm, the amount of movement required for focusing of the object to a change of 1 (m$^{-1}$) in the optical system becomes F$^2$/1000, or 0.4 mm. If, therefore, the flange back length L=15 mm is taken as a compromise value, the flange back length is adjusted with a tolerance of ±2 (m$^{-1}$), which gives the limit of focus adjustment sufficient for the attachment TV camera for endoscopes. Such a construction can also be realized by means other than a prism. For example, the refractive index of an optical member may be changed by making the thickness of glass material constant, or a gradient index optical element may also be used to continuously change the refractive index.

Twelfth Embodiment

The apparatus of this embodiment is adapted to make the focus adjustment without using the auto-iris so far discussed. Although each of the ninth to eleventh embodiments is such that the flange back length is changed by using the auto-iris and reading its driving voltage in order to make the focus adjustment, the twelfth embodiment is designed so that the output voltage from the CCD is directly read and feedback control for the focus adjustment is made in accordance with the signal intensity. Thus, the problem of brightness of the image, because the auto-iris is not used, is solved by using the automatic light control or the electronic shutter for optimum illuminance. The problem of being out of focus, on the other hand, is treated by the flange back adjustment without utilizing the effect of the auto-iris.

The twelfth embodiment, although its pan-focus effect is not very great compared with the case where the auto-iris is used, has a marked effect on the simplification of its mechanical structure, notably on a cost reduction. A flowchart in this case is omitted.

As mentioned above, there is no doubt that each of the ninth to twelfth embodiments, unlike the autofocus technique used in cameras, has a great effect as the principle of the autofocus technique inherent in the endoscope having internal illumination because the brightness of the CCD surface is used as focus detecting means. Furthermore, it facilitates the formation of a hermetical structure and brings about a considerable effect in order to realize the TV camera which can be used in the autoclave.

In this case, because of the transmission characteristics of the endoscope used, the variations of luminance of the light source device, and the difference between the spectral reflectances of the objects to be observed (for example, the interiors of the stomach and the large intestine), the distance x6 forming the boundary between the regions β and γ (where the aperture of the auto-iris 30 is maximized) will be changed. Thus, there is the need to correct the standard of brightness so that the autofocus device is operated at a distance required for a user's observation. In order to make this correction, it is only necessary to change the luminance Bk of the light source. This operation corresponds to the Bk balance of the flowchart shown in FIG. 17.

As stated above, the adapter lens or the CCD is driven in accordance with the voltage value capable of changing the aperture of the auto-iris, and the Bk balance for correcting the luminance Bk of the light source to a constant value is used to obviate the variations of luminance. Thus, the endoscope apparatus of the present invention can secure a high-quality image even in the limit of x>x5 and is more favorable for the use of the AI device.

What is claimed is:

1. An endoscope apparatus comprising:

an optical system for forming an image of an object;

a solid-state image sensor for receiving the image formed by said optical system;

illuminating means for irradiating the object with illuminating light;

light control means for changing brightness of the illuminating light;

stop means whose aperture is variable, disposed in said optical system;

detecting means for detecting brightness of the image of the object; and control means for controlling said stop means and said light control means so that an intensity of a signal output from said solid-state image sensor is kept substantially constant in accordance with brightness information derived from said detecting means.

2. An endoscope apparatus comprising:

an optical system for forming an image of an object;

a solid-state image sensor for receiving the image formed by said optical system;

electric light control means for controlling an amount of electric charges stored in said solid-state image sensor;

stop means whose aperture is variable, disposed in said optical system; and control means for controlling said stop means and said electric light control means so that an intensity of a signal output from said solid-state image sensor is kept substantially constant.

3. An endoscope apparatus comprising:

an optical system for forming an image of an object;

a solid-state image sensor for receiving the image formed by said optical system;

illuminating means for irradiating the object with illuminating light;

detecting means for detecting brightness of the image of the object; and driving means for changing an optical path length between said optical system and said solid-state image sensor in accordance with brightness information derived from said detecting means.

4. An endoscope apparatus according to claim 1, wherein said control means has an operation mode for controlling only said stop means in a state in which an amount of light irradiated from said illuminating means is kept constant.

5. An endoscope apparatus according to claim 1, wherein said control means has an operation mode for controlling only said light control means in a state in which the aperture of said stop means is kept constant.

6. An endoscope apparatus comprising:

an optical system for forming an image of an object;

a solid-state image sensor for receiving the image formed by said optical system;

illuminating means for irradiating the object with illuminating light;

light control means for changing brightness of the illuminating light;

stop means whose aperture is variable, disposed in said optical system;

detecting means for detecting brightness of the image of the object; and control means for controlling said stop means and said light control means so that an intensity of a signal output from said solid-state image sensor is kept substantially constant in accordance with brightness information derived from said detecting means, said control means having a first operation mode for controlling only said stop means in a state in which an amount of light irradiated from said illuminating means is kept constant and a second operation mode for controlling only said light control means in a state in which the aperture of said stop means is kept constant.

7. An endoscope apparatus according to any one of claims 1, 4 or 6, wherein when brightness of said brightness information is less than a predetermined brightness, said control means controls said light control means so that the brightness of the illuminating light increases.

8. An endoscope apparatus according to any one of claims 1, 4 or 6, wherein when brightness of said brightness information is greater than a predetermined brightness, said control means controls said light control means so that the brightness of the illuminating light decreases.

9. An endoscope apparatus according to any one of claims 1, 5 or 6, wherein when brightness of said brightness information is less than a predetermined brightness, said control means controls said stop means so that the aperture of said stop means increases.

10. An endoscope apparatus according to any one of claims 1, 5 or 6, wherein when brightness of said brightness information is greater than a predetermined brightness, said control means controls said stop means so that the aperture of said stop means diminishes.

11. An endoscope apparatus according to any one of claims 1, 4 or 6, wherein when brightness of said brightness information is less than a predetermined brightness, said control means controls said light control means so that the brightness of the illuminating light increases and controls said stop means so that the aperture of said stop means increases, and when the brightness of said brightness information is greater than the predetermined brightness, said control means controls said light control means so that the brightness of the illuminating light decreases and controls said stop means so that the aperture of said stop means diminishes.

12. An endoscope apparatus comprising:

an imaging optical system for forming an image of an object;

a solid-state image sensor for receiving the image formed by said imaging optical system;

a light source device for supplying illuminating light with which the object is illuminated, having light control means for adjusting an amount of light;

an illuminating optical system for irradiating the object with light from said light source device;

stop means whose aperture is variable, disposed in said imaging optical system; and control means for controlling said light control means and said stop means so that an intensity of a signal output from said solid-state image sensor is kept substantially constant.

13. An endoscope apparatus according to claim 12, wherein when the intensity of the signal output from said solid-state image sensor is less than a predetermined brightness, said control means controls said light control means in a state in which the aperture of said stop means is minimized, to increase the amount of light supplied by said light source device, and controls said stop means after the amount of light has been maximized.

14. An endoscope apparatus according to claim 12, wherein when the intensity of the signal output from said solid-state image sensor is greater than a predetermined brightness, said control means controls said stop means so that the aperture of said stop means diminishes in a state in which the amount of light of said light source device is maximized by said light control means and controls said light control means after the aperture has been minimized.

15. An endoscope apparatus according to claim 12, wherein when the intensity of the signal output from said solid-state image sensor is less than a predetermined brightness, said control means controls said light control means in a state in which the aperture of said stop means is minimized, to increase the amount of light supplied by said light source device, and controls said stop means after the amount of light has been maximized, and when the intensity of the signal output from said solid-state image sensor is greater than the predetermined brightness, said control means controls said stop means so that the aperture of said stop means diminishes in a state in which the amount of light of said light source device is maximized by said light control means and controls said light control means after the aperture has been minimized.

16. An endoscope apparatus according to claim 3, wherein said optical system includes stop means whose aperture is variable and control mean for controlling said stop means in accordance with said brightness information, and said driving means is driven in accordance with a signal for controlling said stop means.

17. An endoscope apparatus according to claims 3 or 16, wherein brightness of said brightness information is greater than a predetermined brightness, said driving means drives said optical system and/or said solid-state image sensor so that the optical path length increases.

18. An endoscope apparatus according to claims 3 or 16, wherein brightness of said brightness information is less than a predetermined brightness, said driving means drives said optical system and/or said solid-state image sensor so that the optical path length diminishes.

19. An endoscope apparatus according to any one of claims 5, 6, 13 or 14, wherein said stop means satisfies a condition:

$$\phi 2 \geqq 2.15 \times 10^{-4} F/Px$$

where $\phi 2$ is a minimum aperture of said stop means, F is a focal length of said optical system, and Px is a pixel pitch in a horizontal scanning direction of said solid-state image sensor.

20. An endoscope apparatus according to any one of claims 4, 6 or 13, further comprising electric amplifying means having a function for amplifying a video signal produced based on the signal output from said solid-state image sensor, wherein said control means operates said electric amplifying means after the aperture of said stop means has been maximized and an amount of light supplied by a light source has been maximized by said light control means.

21. An endoscope apparatus according to any one of claims 1–6, 12–16, wherein said control means is a central processing unit.

22. An endoscope apparatus according to claims 3 or 16, wherein when the aperture of said stop means is maximum, a brightness adjustment for correcting brightness to be constant is executed by said light control means.

23. An endoscope apparatus according to claim 20, wherein when an operation of said light control means has been completed, said light control means is controlled to return to an initial mode.

24. An endoscope apparatus according to claim 2, wherein when an intensity of illuminating light is a predetermined value, said control means controls said stop means.

25. An endoscope apparatus according to claim 2, wherein when the aperture of said stop means is a predetermined value, said control means controls said light control means.

26. An endoscope apparatus according to claim 1, further comprising electric light control means for controlling an amount of electric charges stored in said solid-state image sensor, said electric light control means being controlled by said control means.

27. An endoscope apparatus according to claim 26, wherein said control means controls said electric light control means after the aperture of said stop means has been minimized and an amount of light with which the object is irradiated by said illuminating means has been minimized.

28. An endoscope apparatus according to claim 24, wherein said control means is a central processing unit.

29. An endoscope apparatus according to claim 25, wherein said control means is a central processing unit.

* * * * *